(12) United States Patent
Wang et al.

(10) Patent No.: US 6,811,782 B1
(45) Date of Patent: Nov. 2, 2004

(54) PEPTIDE COMPOSITION AS IMMUNOGEN FOR THE TREATMENT OF ALLERGY

(75) Inventors: Chang Yi Wang, Cold Spring Harbor, NY (US); Alan M. Walfield, Huntington Station, NY (US)

(73) Assignee: United Biomedical, Inc., Hauppauge, NY (US)

( * ) Notice: Subject to any disclaimer, the term of this patent is extended or adjusted under 35 U.S.C. 154(b) by 0 days.

(21) Appl. No.: 09/701,623

(22) PCT Filed: Jun. 21, 1999

(86) PCT No.: PCT/US99/13959

§ 371 (c)(1),
(2), (4) Date: Dec. 1, 2000

(87) PCT Pub. No.: WO99/67293

PCT Pub. Date: Dec. 29, 1999

Related U.S. Application Data

(63) Continuation-in-part of application No. 09/100,287, filed on Jun. 20, 1998, now abandoned.

(51) Int. Cl.[7] ...................... A61K 39/385; A61K 39/00; C07K 17/02
(52) U.S. Cl. ................ 424/185.1; 424/193.1; 530/324
(58) Field of Search ................ 530/324; 424/185.1, 424/193, 194.1

(56) References Cited

U.S. PATENT DOCUMENTS 6,025,468 A * 2/2000 Wang et al.
6,228,987 B1 * 5/2001 Wang et al.

FOREIGN PATENT DOCUMENTS

| WO | WO 93/04173 | 3/1993 |
|---|---|---|
| WO | WO 95/26365 | * 10/1995 |
| WO | WO 98/24808 | 6/1998 |

OTHER PUBLICATIONS

Ngo et al., 1994, The Protein Folding Problem and Tertiary Structure Prediction, pp. 492–495.*
Navarro et al, Molec Immunol 32: 1–8, 1995.*
Ghaderi et al, Mol Immunology 30(18): 1655–63, 1993.*
Harlow et al, in Antibodies a Laboratory Manual, 1998, Cold Spring harbor laboratory publication, Cold Spring Harbor, NY, pp. 82–83 and 128–129.*
Kuby et al., 1994, Immunology, second edition, pp. 85–96.*
Abaza et al, J of Protein Chemistry 11(5): 433–444, 1992.*
Nissim et al, J Immunology 150: 1365–74, Feb. 1993.*
B. Helm, et al., *Nature*, 331:180–183 (1988).
D. Vercelli., *Nature*, 338:649–651 (1989).
J. Alexander et al., *Immunity*, 751–761 (1994).
D.S. Burt, et al., *Molecular Immunol.*, 24:379–389 (1987).
D.S. Burt, et al., *Eur. J. Immunol.*, 17:437–440 (1987).
Noriki Nio et al., *Peptide Chemistry*, 1987, 765–768.
Noriki Nio et al., *FEBS*, 1993, 319(3):225–228.
Leonard Presta et al., *J. Biol. Chem.*, 1994, 269(42):26368–26373.
Christoph Heusser et al., *Current Opinion in Immunol.*, 1997, 9(6):805–813.

* cited by examiner

*Primary Examiner*—Christina Chan
*Assistant Examiner*—Phuong N Huynh
(74) *Attorney, Agent, or Firm*—Morgan & Finnegan, LLP

(57) ABSTRACT

The invention provides peptides comprising a sequence homologous to a portion of the third constant domain of the epsilon heavy chain of IgE, covalently linked to either (1) a carrier protein, or (2) a helper T cell epitope, and optionally to other immunostimulatory sequences as well. The invention provides for the use of such peptides as immunogens to elicit the production in mammals of high titer polyclonal antibodies, which are specific to a target effector site on the epsilon heavy chain of IgE. The peptides are expected to be useful in pharmaceutical compositions, to provide an immunotherapy for IgE-mediated allergic diseases.

4 Claims, No Drawings

SEQUENCE LISTING

<160> NUMBER OF SEQ ID NOS: 91

<210> SEQ ID NO 1
<211> LENGTH: 325
<212> TYPE: PRT
<213> ORGANISM: HUMAN
<220> FEATURE:
<223> OTHER INFORMATION: CH2CH3 of human IgE
<300> PUBLICATION INFORMATION:
<301> AUTHORS: Dorrington,
      Bennich,
<303> JOURNAL: Immunology
<304> VOLUME: 41
<306> PAGES: 3-25
<307> DATE: 1978

<400> SEQUENCE: 1

Val Cys Ser Arg Asp Phe Thr Pro Pro Thr Val Lys Ile Leu Gln Ser
 1               5                  10                  15

Ser Cys Asp Gly Gly Gly His Phe Pro Pro Thr Ile Gln Leu Leu Cys
                20                  25                  30

Leu Val Ser Gly Tyr Thr Pro Gly Thr Ile Asn Ile Thr Trp Leu Glu
            35                  40                  45

Asp Gly Gln Val Met Asp Val Asp Leu Ser Thr Ala Ser Thr Thr Gln
        50                  55                  60

Glu Gly Glu Leu Ala Ser Thr Gln Ser Glu Leu Thr Leu Ser Gln Lys
 65                  70                  75                  80

His Trp Leu Ser Asp Arg Thr Tyr Thr Cys Gln Val Thr Tyr Gln Gly
                85                  90                  95

His Thr Phe Glu Asp Ser Thr Lys Lys Cys Ala Asp Ser Asn Pro Arg
            100                 105                 110

Gly Val Ser Ala Tyr Leu Ser Arg Pro Ser Pro Phe Asp Leu Phe Ile
        115                 120                 125

Arg Lys Ser Pro Thr Ile Thr Cys Leu Val Val Asp Leu Ala Pro Ser
        130                 135                 140

-continued

```
Lys Gly Thr Val Asn Leu Thr Trp Ser Arg Ala Ser Gly Lys Pro Val
145                 150                 155                 160

Asn His Ser Thr Arg Lys Glu Glu Lys Gln Arg Asn Gly Thr Leu Thr
                165                 170                 175

Val Thr Ser Thr Leu Pro Val Gly Thr Arg Asp Trp Ile Glu Gly Glu
            180                 185                 190

Thr Tyr Gln Cys Arg Val Thr His Pro His Leu Pro Arg Ala Leu Met
        195                 200                 205

Arg Ser Thr Thr Lys Thr Ser Gly Pro Arg Ala Pro Glu Val Tyr
210                 215                 220

Ala Phe Ala Thr Pro Glu Trp Pro Gly Ser Arg Asp Lys Arg Thr Leu
225                 230                 235                 240

Ala Cys Leu Ile Gln Asn Phe Met Pro Glu Asp Ile Ser Val Gln Trp
                245                 250                 255

Leu His Asn Glu Val Gln Leu Pro Asp Ala Arg His Ser Thr Thr Gln
                260                 265                 270

Pro Arg Lys Thr Lys Gly Ser Gly Phe Phe Val Phe Ser Arg Leu Glu
            275                 280                 285

Val Thr Arg Ala Glu Trp Gln Glu Lys Asp Glu Phe Ile Cys Arg Ala
        290                 295                 300

Val His Glu Ala Ala Ser Pro Ser Gln Thr Val Gln Arg Ala Val Ser
305                 310                 315                 320

Val Asn Pro Gly Lys
                325
```

<210> SEQ ID NO 2
<211> LENGTH: 312
<212> TYPE: PRT
<213> ORGANISM: Dog
<220> FEATURE:
<223> OTHER INFORMATION: CH2CH3n of dog IgE
<300> PUBLICATION INFORMATION:
<301> AUTHORS: Patel,
<303> JOURNAL: Immunogenetics
<304> VOLUME: 41
<306> PAGES: 282-286
<307> DATE: 1995

<400> SEQUENCE: 2

```
Ala Cys Ala Leu Asn Phe Ile Pro Pro Thr Val Lys Leu Phe His Ser
 1               5                  10                  15

Ser Cys Asn Pro Val Gly Asp Thr His Thr Thr Ile Gln Leu Leu Cys
            20                  25                  30

Leu Ile Ser Gly Tyr Val Pro Gly Asp Met Glu Val Ile Trp Leu Val
        35                  40                  45

Asp Gly Gln Lys Ala Thr Asn Ile Phe Pro Tyr Thr Ala Pro Gly Thr
    50                  55                  60

Lys Glu Gly Asn Val Thr Ser Thr His Ser Glu Leu Asn Ile Thr Gln
65                  70                  75                  80

Gly Glu Trp Val Ser Gln Lys Thr Tyr Thr Cys Gln Gly Phe Thr Phe
                85                  90                  95

Lys Asp Glu Ala Arg Lys Cys Ser Glu Ser Asp Pro Arg Gly Val Thr
            100                 105                 110

Ser Tyr Leu Ser Pro Pro Ser Pro Leu Asp Leu Tyr Val His Lys Ala
        115                 120                 125

Pro Lys Ile Thr Cys Leu Val Val Asp Leu Ala Thr Met Glu Gly Met
    130                 135                 140
```

```
Asn Leu Thr Trp Tyr Arg Glu Ser Lys Glu Pro Val Asn Pro Gly Pro
145                 150                 155                 160

Leu Asn Lys Lys Asp His Phe Asn Gly Thr Ile Thr Val Thr Ser Thr
                165                 170                 175

Leu Pro Val Asn Thr Asn Asp Trp Ile Glu Gly Glu Thr Tyr Tyr Cys
            180                 185                 190

Arg Val Thr His Pro His Leu Pro Lys Asp Ile Val Arg Ser Ile Ala
            195                 200                 205

Lys Ala Pro Gly Lys Arg Ala Pro Pro Asp Val Tyr Leu Phe Leu Pro
210                 215                 220

Pro Glu Glu Gln Gly Thr Lys Asp Arg Val Thr Leu Thr Cys Leu
225                 230                 235                 240

Ile Gln Asn Phe Phe Pro Ala Asp Ile Ser Val Gln Trp Leu Arg Asn
                245                 250                 255

Asp Ser Pro Ile Gln Thr Asp Gln Tyr Thr Thr Thr Gly Pro His Lys
            260                 265                 270

Val Ser Gly Ser Arg Pro Ala Phe Phe Ile Phe Ser Arg Leu Glu Val
            275                 280                 285

Ser Arg Val Asp Trp Glu Gln Lys Asn Lys Phe Thr Cys Gln Val Val
    290                 295                 300

His Glu Ala Leu Ser Gly Ser Arg
305                 310
```

<210> SEQ ID NO 3
<211> LENGTH: 313
<212> TYPE: PRT
<213> ORGANISM: RAT
<220> FEATURE:
<223> OTHER INFORMATION: CH2CH3 of rat IgE
<300> PUBLICATION INFORMATION:
<301> AUTHORS: Dorrington,
      Bennich,
<303> JOURNAL: Immunology
<304> VOLUME: 41
<306> PAGES: 3-25
<307> DATE: 1978
<300> PUBLICATION INFORMATION:
<301> AUTHORS: Patel,
<303> JOURNAL: Immunogenetics
<304> VOLUME: 41
<306> PAGES: 282-286
<307> DATE: 1995
<300> PUBLICATION INFORMATION:
<301> AUTHORS: Steen,
<303> JOURNAL: J. Mol. Biol.
<304> VOLUME: 177
<306> PAGES: 19-32
<307> DATE: 1984
<300> PUBLICATION INFORMATION:
<301> AUTHORS: Ishida,
<303> JOURNAL: EMBO J.
<304> VOLUME: 1
<306> PAGES: 1117-1123
<307> DATE: 1982

<400> SEQUENCE: 3

```
Ala Arg Pro Val Asn Ile Thr Lys Pro Thr Val Asp Leu Leu His Ser
1               5                   10                  15

Ser Cys Asp Pro Asn Ala Phe His Ser Thr Ile Gln Leu Tyr Cys Phe
            20                  25                  30

Val Tyr Gly His Ile Gln Asn Asp Val Ser Ile His Trp Leu Met Asp
            35                  40                  45

Asp Arg Lys Ile Tyr Asp Thr His Ala Gln Asn Val Leu Ile Lys Glu
```

-continued

```
                50                   55                    60
Glu Gly Lys Leu Ala Ser Thr Tyr Ser Arg Leu Asn Ile Thr Gln Gln
 65                  70                  75                  80

Gln Trp Met Ser Glu Ser Thr Phe Thr Cys Lys Val Thr Ser Gln Gly
                 85                  90                  95

Glu Asn Tyr Trp Ala His Thr Arg Arg Cys Ser Asp Asp Glu Pro Arg
                100                 105                 110

Gly Val Ile Thr Tyr Leu Ile Pro Pro Ser Pro Leu Asp Leu Tyr Glu
                115                 120                 125

Asn Gly Thr Pro Lys Leu Thr Cys Leu Val Leu Asp Leu Glu Ser Glu
130                 135                 140

Glu Asn Ile Thr Val Thr Trp Val Arg Glu Arg Lys Lys Ser Ile Gly
145                 150                 155                 160

Ser Ala Ser Gln Arg Ser Thr Lys His His Asn Ala Thr Thr Ser Ile
                165                 170                 175

Thr Ser Ile Leu Pro Val Asp Ala Lys Asp Trp Ile Glu Gly Glu Gly
                180                 185                 190

Tyr Gln Cys Arg Val Asp His Pro His Phe Pro Lys Pro Ile Val Arg
                195                 200                 205

Ser Ile Thr Lys Ala Leu Gly Leu Arg Ser Ala Pro Glu Val Tyr Val
210                 215                 220

Phe Leu Pro Pro Glu Glu Glu Lys Asn Lys Arg Thr Leu Thr Cys
225                 230                 235                 240

Leu Ile Gln Asn Phe Phe Pro Glu Asp Ile Ser Val Gln Trp Leu Gln
                245                 250                 255

Asp Ser Lys Leu Ile Pro Lys Ser Gln His Ser Thr Thr Thr Pro Leu
                260                 265                 270

Lys Thr Asn Gly Ser Asn Gln Arg Phe Phe Ile Phe Ser Arg Leu Glu
                275                 280                 285

Val Thr Lys Ala Leu Trp Thr Gln Thr Lys Gln Phe Thr Cys Arg Val
290                 295                 300

Ile His Glu Ala Leu Arg Glu Pro Arg
305                 310
```

<210> SEQ ID NO 4
<211> LENGTH: 313
<212> TYPE: PRT
<213> ORGANISM: MOUSE
<220> FEATURE:
<223> OTHER INFORMATION: CH2CH3 of mouse IgE

<400> SEQUENCE: 4

```
Val Arg Pro Val Thr His Ser Leu Ser Pro Pro Trp Ser Tyr Ser Ile
 1               5                   10                  15

His Arg Cys Asp Pro Asn Ala Phe His Ser Thr Ile Gln Leu Tyr Cys
                20                  25                  30

Phe Ile Tyr Gly His Ile Leu Asn Asp Val Ser Val Ser Trp Leu Met
                35                  40                  45

Asp Asp Arg Glu Ile Thr Asp Thr Leu Ala Gln Thr Val Leu Ile Lys
 50                  55                  60

Glu Glu Gly Lys Leu Ala Ser Thr Cys Ser Lys Leu Asn Ile Thr Glu
 65                  70                  75                  80

Gln Gln Trp Met Ser Glu Ser Thr Phe Thr Cys Arg Val Thr Ser Gln
                 85                  90                  95

Gly Cys Asp Tyr Leu Ala His Thr Arg Arg Cys Pro Asp His Glu Pro
```

```
                    100                 105                 110
Arg Gly Ala Ile Thr Tyr Leu Ile Pro Pro Ser Pro Leu Asp Leu Tyr
        115                 120                 125

Gln Asn Gly Ala Pro Lys Leu Thr Cys Leu Val Val Asp Leu Glu Ser
130                 135                 140

Glu Lys Asn Val Asn Val Thr Trp Asn Gln Glu Lys Lys Thr Ser Val
145                 150                 155                 160

Ser Ala Ser Gln Trp Tyr Thr Lys His His Asn Asn Ala Thr Thr Ser
                165                 170                 175

Ile Thr Ser Ile Leu Pro Val Val Ala Lys Asp Trp Ile Glu Gly Tyr
            180                 185                 190

Gly Tyr Gln Cys Ile Val Asp Arg Pro Asp Phe Pro Lys Pro Ile Val
        195                 200                 205

Arg Ser Ile Thr Lys Thr Pro Gly Gln Arg Ser Ala Pro Glu Val Tyr
    210                 215                 220

Val Phe Pro Pro Glu Glu Glu Ser Glu Asp Lys Arg Thr Leu Thr
225                 230                 235                 240

Cys Leu Ile Gln Asn Phe Phe Pro Glu Asp Ile Ser Val Gln Trp Leu
                245                 250                 255

Gly Asp Gly Lys Leu Ile Ser Asn Ser Gln His Ser Thr Thr Thr Pro
            260                 265                 270

Leu Lys Ser Asn Gly Asn Gln Gly Phe Ile Phe Ser Arg Leu Glu
    275                 280                 285

Val Ala Lys Thr Leu Trp Thr Gln Arg Lys Gln Phe Thr Cys Gln Val
        290                 295                 300

Ile His Glu Ala Leu Gln Lys Pro Arg
305                 310

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 5

Cys Gly Glu Thr Tyr Gln Ser Arg Val Thr His Pro His Leu Pro Arg
  1               5                  10                  15

Ala Leu Met Arg Ser Thr Thr Lys Cys
                20                  25

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 6

Cys Gly Glu Thr Tyr Tyr Ser Arg Val Thr His Pro His Leu Pro Lys
  1               5                  10                  15

Asp Ile Val Arg Ser Ile Ala Lys Cys
                20                  25

<210> SEQ ID NO 7
<211> LENGTH: 25
<212> TYPE: PRT
```

```
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 7

Cys Gly Glu Gly Tyr Gln Ser Arg Val Asp His Pro His Phe Pro Lys
 1               5                  10                  15

Pro Ile Val Arg Ser Ile Thr Lys Cys
            20                  25

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 8

Cys Gly Tyr Gly Tyr Gln Ser Ile Val Asp Arg Pro Asp Phe Pro Lys
 1               5                  10                  15

Pro Ile Val Arg Ser Ile Thr Leu Cys
            20                  25

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 9

Lys Lys Lys Ile Ile Thr Ile Thr Arg Ile Ile Thr Ile Ile Thr Thr
 1               5                  10                  15

Ile Asp

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: ()..)
<223> OTHER INFORMATION: I, M, L
<221> NAME/KEY: MOD_RES
<222> LOCATION: (2)
<223> OTHER INFORMATION: S, T
<221> NAME/KEY: MOD_RES
<222> LOCATION: (5)
<223> OTHER INFORMATION: K, R
<221> NAME/KEY: MOD_RES
<222> LOCATION: (6)
<223> OTHER INFORMATION: G, T
<221> NAME/KEY: MOD_RES
<222> LOCATION: (10)
<223> OTHER INFORMATION: H, T
<221> NAME/KEY: MOD_RES
<222> LOCATION: (11)
<223> OTHER INFORMATION: K, R
<221> NAME/KEY: MOD_RES
<222> LOCATION: (12)
<223> OTHER INFORMATION: I, M, L
<221> NAME/KEY: MOD_RES
<222> LOCATION: (14)
<223> OTHER INFORMATION: G, T
<221> NAME/KEY: MOD_RES
```

```
<222> LOCATION: (15)
<223> OTHER INFORMATION: I, M, V
<221> NAME/KEY: MOD_RES
<222> LOCATION: (2)

<400> SEQUENCE: 10

Xaa Xaa Glu Ile Xaa Xaa Val Ile Val Xaa Xaa Xaa Glu Xaa Xaa
 1               5                  10                  15

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: (3)
<223> OTHER INFORMATION: I, M, L
<221> NAME/KEY: MOD_RES
<222> LOCATION: (4)
<223> OTHER INFORMATION: S, T
<221> NAME/KEY: MOD_RES
<222> LOCATION: (7)
<223> OTHER INFORMATION: K, R
<221> NAME/KEY: MOD_RES
<222> LOCATION: (8)
<223> OTHER INFORMATION: G, T
<221> NAME/KEY: MOD_RES
<222> LOCATION: (12)
<223> OTHER INFORMATION: H, T
<221> NAME/KEY: MOD_RES
<222> LOCATION: (13)
<223> OTHER INFORMATION: K, R
<221> NAME/KEY: MOD_RES
<222> LOCATION: (14)
<223> OTHER INFORMATION: I, M, L
<221> NAME/KEY: MOD_RES
<222> LOCATION: (16)
<223> OTHER INFORMATION: G, T
<221> NAME/KEY: MOD_RES
<222> LOCATION: (17)
<223> OTHER INFORMATION: I, M, L

<400> SEQUENCE: 11

Ile Ser Xaa Xaa Glu Ile Xaa Xaa Val Ile Val Xaa Xaa Xaa Glu Xaa
 1               5                  10                  15

Xaa Leu Phe

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 12

Thr Ile Asn Lys Pro Lys Gly Tyr Val Gly Lys Glu
 1               5                  10

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 13

Thr Ala Lys Ser Lys Lys Phe Pro Ser Tyr Thr Ala Thr Tyr Gln Phe
```

<210> SEQ ID NO 14
<211> LENGTH: 45
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 14

Lys Lys Lys Ile Ile Thr Ile Thr Arg Ile Ile Thr Ile Ile Thr Thr
1               5                   10                  15

Ile Asp Gly Gly Cys Gly Glu Thr Tyr Gln Ser Arg Val Thr His Pro
            20                  25                  30

His Leu Pro Arg Ala Leu Met Arg Ser Thr Thr Lys Cys
        35                  40                  45

<210> SEQ ID NO 15
<211> LENGTH: 63
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 15

Thr Ala Lys Ser Lys Lys Phe Pro Ser Tyr Thr Ala Thr Tyr Gln Phe
1               5                   10                  15

Gly Gly Lys Lys Lys Ile Ile Thr Ile Thr Arg Ile Ile Thr Ile Ile
            20                  25                  30

Thr Thr Ile Asp Gly Gly Cys Gly Glu Thr Tyr Gln Ser Arg Val Thr
        35                  40                  45

His Pro His Leu Pro Arg Ala Leu Met Arg Ser Thr Thr Lys Cys
    50                  55                  60

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: UNSURE
<222> LOCATION: (3)
<223> OTHER INFORMATION: any amino acid except proline
<221> NAME/KEY: UNSURE
<222> LOCATION: (5)
<223> OTHER INFORMATION: any amino acid except proline

<400> SEQUENCE: 16

Pro Pro Xaa Pro Xaa Pro
1               5

<210> SEQ ID NO 17
<211> LENGTH: 59
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 17

Thr Ile Asn Lys Pro Lys Gly Tyr Val Gly Lys Glu Gly Gly Lys Lys
1               5                   10                  15

Lys Ile Ile Thr Ile Thr Arg Ile Ile Thr Ile Ile Thr Thr Ile Asp
             20                  25                  30

Gly Gly Cys Gly Glu Thr Tyr Gln Ser Arg Val Thr His Pro His Leu
             35                  40                  45

Pro Arg Ala Leu Met Arg Ser Thr Thr Lys Cys
             50                  55

<210> SEQ ID NO 18
<211> LENGTH: 46
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: (4)
<223> OTHER INFORMATION: S, T
<221> NAME/KEY: MOD_RES
<222> LOCATION: (7)
<223> OTHER INFORMATION: K, R
<221> NAME/KEY: MOD_RES
<222> LOCATION: (8)
<223> OTHER INFORMATION: G, T
<221> NAME/KEY: MOD_RES
<222> LOCATION: (12)
<223> OTHER INFORMATION: H, T
<221> NAME/KEY: MOD_RES
<222> LOCATION: (13)
<223> OTHER INFORMATION: K, R
<221> NAME/KEY: MOD_RES
<222> LOCATION: (16)
<223> OTHER INFORMATION: G, T

<400> SEQUENCE: 18

Ile Ser Ile Xaa Glu Ile Xaa Xaa Val Ile Val Xaa Xaa Ile Glu Xaa
 1               5                  10                  15

Ile Leu Phe Gly Gly Cys Gly Glu Thr Tyr Gln Ser Arg Val Thr His
             20                  25                  30

Pro His Leu Pro Arg Ala Leu Met Arg Ser Thr Thr Lys Cys
             35                  40                  45

<210> SEQ ID NO 19
<211> LENGTH: 63
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: (21)
<223> OTHER INFORMATION: S, T
<221> NAME/KEY: MOD_RES
<222> LOCATION: (24)
<223> OTHER INFORMATION: K, R
<221> NAME/KEY: MOD_RES
<222> LOCATION: (25)
<223> OTHER INFORMATION: G, T
<221> NAME/KEY: MOD_RES
<222> LOCATION: (29)
<223> OTHER INFORMATION: H, T
<221> NAME/KEY: MOD_RES
<222> LOCATION: (30)
<223> OTHER INFORMATION: K, R
<221> NAME/KEY: MOD_RES
<222> LOCATION: (33)
<223> OTHER INFORMATION: G, T

<400> SEQUENCE: 19

Thr Ala Lys Ser Lys Lys Phe Pro Ser Tyr Thr Ala Thr Gln Phe Gly
 1               5                  10                  15

Gly Ile Ser Ile Xaa Glu Ile Xaa Xaa Val Ile Val Xaa Xaa Ile Glu
                20                  25                  30

Xaa Ile Leu Phe Gly Gly Cys Gly Glu Thr Tyr Gln Ser Arg Val Thr
        35                  40                  45

His Pro His Leu Pro Arg Ala Leu Met Arg Ser Thr Thr Lys Cys
    50                  55                  60

<210> SEQ ID NO 20
<211> LENGTH: 60
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: (18)
<223> OTHER INFORMATION: S, T
<221> NAME/KEY: MOD_RES
<222> LOCATION: (21)
<223> OTHER INFORMATION: K, R
<221> NAME/KEY: MOD_RES
<222> LOCATION: (22)
<223> OTHER INFORMATION: G, T
<221> NAME/KEY: MOD_RES
<222> LOCATION: (26)
<223> OTHER INFORMATION: H, T
<221> NAME/KEY: MOD_RES
<222> LOCATION: (27)
<223> OTHER INFORMATION: K, R
<221> NAME/KEY: MOD_RES
<222> LOCATION: (30)
<223> OTHER INFORMATION: G, T

<400> SEQUENCE: 20

Thr Ile Asn Lys Pro Lys Gly Tyr Val Gly Lys Glu Gly Gly Ile Ser
  1               5                  10                  15

Ile Xaa Glu Ile Xaa Xaa Val Ile Val Xaa Xaa Ile Glu Xaa Ile Leu
                20                  25                  30

Phe Gly Gly Cys Gly Glu Thr Tyr Gln Ser Arg Val Thr His Pro His
        35                  40                  45

Leu Pro Arg Ala Leu Met Arg Ser Thr Thr Lys Cys
    50                  55                  60

<210> SEQ ID NO 21
<211> LENGTH: 42
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: (1)
<223> OTHER INFORMATION: I, M, L
<221> NAME/KEY: MOD_RES
<222> LOCATION: (2)
<223> OTHER INFORMATION: S, T
<221> NAME/KEY: MOD_RES
<222> LOCATION: (5)
<223> OTHER INFORMATION: K, R
<221> NAME/KEY: MOD_RES
<222> LOCATION: (6)
<223> OTHER INFORMATION: G, T
<221> NAME/KEY: MOD_RES
<222> LOCATION: (10)
<223> OTHER INFORMATION: H, T
<221> NAME/KEY: MOD_RES
<222> LOCATION: (11)
<223> OTHER INFORMATION: K, R
<221> NAME/KEY: MOD_RES
<222> LOCATION: (12)
<223> OTHER INFORMATION: I, M, L

```
<221> NAME/KEY: MOD_RES
<222> LOCATION: (14)
<223> OTHER INFORMATION: G, T
<221> NAME/KEY: MOD_RES
<222> LOCATION: (15)
<223> OTHER INFORMATION: I, M, V

<400> SEQUENCE: 21

Xaa Xaa Glu Ile Xaa Xaa Val Ile Val Xaa Xaa Glu Xaa Xaa Gly
 1               5                  10                  15

Gly Cys Gly Glu Thr Tyr Gln Ser Arg Val Thr His Pro His Leu Pro
            20                  25                  30

Arg Ala Leu Met Arg Ser Thr Thr Lys Cys
        35                  40

<210> SEQ ID NO 22
<211> LENGTH: 60
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: (19)
<223> OTHER INFORMATION: I, M, L
<221> NAME/KEY: MOD_RES
<222> LOCATION: (20)
<223> OTHER INFORMATION: S, T
<221> NAME/KEY: MOD_RES
<222> LOCATION: (23)
<223> OTHER INFORMATION: K, R
<221> NAME/KEY: MOD_RES
<222> LOCATION: (24)
<223> OTHER INFORMATION: G, T
<221> NAME/KEY: MOD_RES
<222> LOCATION: (28)
<223> OTHER INFORMATION: H, T
<221> NAME/KEY: MOD_RES
<222> LOCATION: (29)
<223> OTHER INFORMATION: K, R
<221> NAME/KEY: MOD_RES
<222> LOCATION: (30)
<223> OTHER INFORMATION: I, M, L
<221> NAME/KEY: MOD_RES
<222> LOCATION: (32)
<223> OTHER INFORMATION: G, T
<221> NAME/KEY: MOD_RES
<222> LOCATION: (33)
<223> OTHER INFORMATION: I, M, V

<400> SEQUENCE: 22

Thr Ala Lys Ser Lys Lys Phe Pro Ser Tyr Thr Ala Thr Tyr Gln Phe
 1               5                  10                  15

Gly Gly Xaa Xaa Glu Ile Xaa Xaa Val Ile Val Xaa Xaa Glu Xaa
            20                  25                  30

Xaa Gly Gly Cys Gly Glu Thr Tyr Gln Ser Arg Val Thr His Pro His
        35                  40                  45

Leu Pro Arg Ala Leu Met Arg Ser Thr Thr Lys Cys
    50                  55                  60

<210> SEQ ID NO 23
<211> LENGTH: 56
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: (15)
<223> OTHER INFORMATION: I, M, L
```

-continued

```
<221> NAME/KEY: MOD_RES
<222> LOCATION: (16)
<223> OTHER INFORMATION: S, T
<221> NAME/KEY: MOD_RES
<222> LOCATION: (19)
<223> OTHER INFORMATION: K, R
<221> NAME/KEY: MOD_RES
<222> LOCATION: (20)
<223> OTHER INFORMATION: G, T
<221> NAME/KEY: MOD_RES
<222> LOCATION: (24)
<223> OTHER INFORMATION: H, T
<221> NAME/KEY: MOD_RES
<222> LOCATION: (25)
<223> OTHER INFORMATION: K, R
<221> NAME/KEY: MOD_RES
<222> LOCATION: (26)
<223> OTHER INFORMATION: I, M, L
<221> NAME/KEY: MOD_RES
<222> LOCATION: (28)
<223> OTHER INFORMATION: G, T
<221> NAME/KEY: MOD_RES
<222> LOCATION: (29)
<223> OTHER INFORMATION: I, M, V

<400> SEQUENCE: 23

Thr Ile Asn Lys Pro Lys Gly Tyr Val Gly Lys Glu Gly Gly Xaa Xaa
 1               5                  10                  15

Glu Ile Xaa Xaa Val Ile Val Xaa Xaa Xaa Glu Xaa Xaa Gly Gly Cys
            20                  25                  30

Gly Glu Thr Tyr Gln Ser Arg Val Thr His Pro His Leu Pro Arg Ala
        35                  40                  45

Leu Met Arg Ser Thr Thr Lys Cys
 50                  55

<210> SEQ ID NO 24
<211> LENGTH: 46
<212> TYPE: PRT
<213> ORGANISM: Artificial Sequence
<220> FEATURE:
<223> OTHER INFORMATION: Description of Artificial Sequence: Peptides
      synthesized from amino acids with no genetic material as source
<221> NAME/KEY: MOD_RES
<222> LOCATION: (4)
<223> OTHER INFORMATION: S, T
<221> NAME/KEY: MOD_RES
<222> LOCATION: (7)
<223> OTHER INFORMATION: K, R
<221> NAME/KEY: MOD_RES
<222> LOCATION: (8)
<223> OTHER INFORMATION: G, T
<221> NAME/KEY: MOD_RES
<222> LOCATION: (12)
<223> OTHER INFORMATION: H, T
<221> NAME/KEY: MOD_RES
<222> LOCATION: (13)
<223> OTHER INFORMATION: K, R
<221> NAME/KEY: MOD_RES
<222> LOCATION: (16)
<223> OTHER INFORMATION: G, T

<400> SEQUENCE: 24

Ile Ser Ile Xaa Glu Ile Xaa Xaa Val Ile Val Xaa Xaa Ile Glu Xaa
 1               5                  10                  15

Ile Leu Phe Gly Gly Cys Gly Tyr Gly Tyr Gln Ser Ile Val Asp His
            20                  25                  30

Pro Asp Phe Pro Lys Pro Ile Val Arg Ser Ile Thr Lys Cys
        35                  40                  45

<210> SEQ ID NO 25
```

```
<211> LENGTH: 45
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 25

Lys Lys Lys Ile Ile Thr Ile Thr Arg Ile Ile Thr Ile Ile Thr Thr
 1               5                  10                  15

Ile Asp Gly Gly Cys Gly Tyr Gly Tyr Gln Ser Ile Val Asp His Pro
            20                  25                  30

Asp Phe Pro Lys Pro Ile Val Arg Ser Ile Thr Lys Cys
        35                  40                  45

<210> SEQ ID NO 26
<211> LENGTH: 45
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 26

Lys Lys Lys Ile Ile Thr Ile Thr Arg Ile Ile Thr Ile Ile Thr Thr
 1               5                  10                  15

Ile Asp Gly Gly Cys Gly Glu Thr Tyr Tyr Ser Arg Val Thr His Pro
            20                  25                  30

His Leu Pro Lys Asp Ile Val Arg Ser Ile Ala Lys Cys
        35                  40                  45

<210> SEQ ID NO 27
<211> LENGTH: 46
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: (1)
<223> OTHER INFORMATION: I, M, L
<221> NAME/KEY: MOD_RES
<222> LOCATION: (2)
<223> OTHER INFORMATION: S, T
<221> NAME/KEY: MOD_RES
<222> LOCATION: (7)
<223> OTHER INFORMATION: K, L
<221> NAME/KEY: MOD_RES
<222> LOCATION: (8)
<223> OTHER INFORMATION: G, R
<221> NAME/KEY: MOD_RES
<222> LOCATION: (9)
<223> OTHER INFORMATION: V, T
<221> NAME/KEY: MOD_RES
<222> LOCATION: (10)
<223> OTHER INFORMATION: I, V
<221> NAME/KEY: MOD_RES
<222> LOCATION: (14)
<223> OTHER INFORMATION: I, T
<221> NAME/KEY: MOD_RES
<222> LOCATION: (15)
<223> OTHER INFORMATION: E, R
<221> NAME/KEY: MOD_RES
<222> LOCATION: (16)
<223> OTHER INFORMATION: G, M
<221> NAME/KEY: MOD_RES
<222> LOCATION: (19)
<223> OTHER INFORMATION: F, T
<221> NAME/KEY: MOD_RES
<222> LOCATION: (20)
<223> OTHER INFORMATION: G, M
```

-continued

```
<400> SEQUENCE: 27

Xaa Xaa Ile Ser Glu Ile Xaa Gly Val Xaa Val His Lys Xaa Xaa Xaa
 1               5                  10                  15

Ile Leu Xaa Xaa Gly Cys Gly Glu Thr Tyr Tyr Ser Arg Val Thr His
            20                  25                  30

Pro His Leu Pro Lys Asp Ile Val Arg Ser Ile Ala Lys Cys
        35                  40                  45

<210> SEQ ID NO 28
<211> LENGTH: 49
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 28

Cys Ala Asp Ser Asn Pro Arg Gly Val Ser Ala Tyr Leu Ser Arg Pro
 1               5                  10                  15

Ser Pro Phe Asp Leu Phe Ile Arg Lys Ser Pro Thr Ile Thr Ser Leu
            20                  25                  30

Val Val Asp Leu Ala Pro Ser Lys Gly Thr Val Asn Leu Thr Trp Ser
        35                  40                  45

Arg

<210> SEQ ID NO 29
<211> LENGTH: 60
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 29

Gln Gly His Thr Phe Glu Asp Ser Thr Lys Lys Cys Ala Asp Ser Asn
 1               5                  10                  15

Pro Arg Gly Val Ser Ala Tyr Leu Ser Arg Pro Ser Pro Phe Asp Leu
            20                  25                  30

Phe Ile Arg Lys Ser Pro Thr Ile Thr Ser Leu Val Val Asp Leu Ala
        35                  40                  45

Pro Ser Lys Gly Thr Val Asn Leu Thr Trp Ser Arg
    50                  55                  60

<210> SEQ ID NO 30
<211> LENGTH: 64
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 30

Gln Val Thr Tyr Gln Gly His Thr Phe Glu Asp Ser Thr Lys Lys Cys
 1               5                  10                  15

Ala Asp Ser Asn Pro Arg Gly Val Ser Ala Tyr Leu Ser Arg Pro Ser
            20                  25                  30

Pro Phe Asp Leu Phe Ile Arg Lys Ser Pro Thr Ile Thr Ser Leu Val
        35                  40                  45

Val Asp Leu Ala Pro Ser Lys Gly Thr Val Asn Leu Thr Trp Ser Arg
    50                  55                  60
```

<210> SEQ ID NO 31
<211> LENGTH: 76
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 31

Gln Lys His Trp Leu Ser Asp Arg Thr Tyr Thr Ser Gln Val Thr Tyr
 1               5                  10                  15

Gln Gly His Thr Phe Glu Asp Ser Thr Lys Lys Cys Ala Asp Ser Asn
            20                  25                  30

Pro Arg Gly Val Ser Ala Tyr Leu Ser Arg Pro Ser Pro Phe Asp Leu
        35                  40                  45

Phe Ile Arg Lys Ser Pro Thr Ile Thr Ser Leu Val Val Asp Leu Ala
    50                  55                  60

Pro Ser Lys Gly Thr Val Asn Leu Thr Trp Ser Arg
65                  70                  75

<210> SEQ ID NO 32
<211> LENGTH: 35
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 32

Cys Ala Asp Ser Asn Pro Arg Gly Val Ser Ala Tyr Leu Ser Arg Pro
 1               5                  10                  15

Ser Pro Phe Asp Leu Phe Ile Arg Lys Ser Pro Thr Ile Thr Ser Leu
            20                  25                  30

Val Val Asp
        35

<210> SEQ ID NO 33
<211> LENGTH: 46
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 33

Gln Gly His Thr Phe Glu Asp Ser Thr Lys Lys Cys Ala Asp Ser Asn
 1               5                  10                  15

Pro Arg Gly Val Ser Ala Tyr Leu Ser Arg Pro Ser Pro Phe Asp Leu
            20                  25                  30

Phe Ile Arg Lys Ser Pro Thr Ile Thr Ser Leu Val Val Asp
        35                  40                  45

<210> SEQ ID NO 34
<211> LENGTH: 50
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 34

Gln Val Thr Tyr Gln Gly His Thr Phe Glu Asp Ser Thr Lys Lys Cys

```
                    1               5                  10                 15
Ala Asp Ser Asn Pro Arg Gly Val Ser Ala Tyr Leu Ser Arg Pro Ser
                        20                 25                 30

Pro Phe Asp Leu Phe Ile Arg Lys Ser Pro Thr Ile Thr Ser Leu Val
            35                 40                 45

Val Asp
    50
```

<210> SEQ ID NO 35
<211> LENGTH: 62
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 35

```
Gln Lys His Trp Leu Ser Asp Arg Thr Tyr Thr Ser Gln Val Thr Tyr
  1               5                  10                 15

Gln Gly His Thr Phe Glu Asp Ser Thr Lys Lys Cys Ala Asp Ser Asn
                 20                 25                 30

Pro Arg Gly Val Ser Ala Tyr Leu Ser Arg Pro Ser Pro Phe Asp Leu
             35                 40                 45

Phe Ile Arg Lys Ser Pro Thr Ile Thr Ser Leu Val Val Asp
         50                 55                 60
```

<210> SEQ ID NO 36
<211> LENGTH: 29
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 36

```
Cys Ala Asp Ser Asn Pro Arg Gly Val Ser Ala Tyr Leu Ser Arg Pro
  1               5                  10                 15

Ser Pro Phe Asp Leu Phe Ile Arg Lys Ser Pro Thr Ile
                 20                 25
```

<210> SEQ ID NO 37
<211> LENGTH: 40
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 37

```
Gln Gly His Thr Phe Glu Asp Ser Thr Lys Lys Cys Ala Asp Ser Asn
  1               5                  10                 15

Pro Arg Gly Val Ser Ala Tyr Leu Ser Arg Pro Ser Pro Phe Asp Leu
                 20                 25                 30

Phe Ile Arg Lys Ser Pro Thr Ile
             35                 40
```

<210> SEQ ID NO 38
<211> LENGTH: 44
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 38

Gln Val Thr Tyr Gln Gly His Thr Phe Glu Asp Ser Thr Lys Lys Cys
1               5                   10                  15

Ala Asp Ser Asn Pro Arg Gly Val Ser Ala Tyr Leu Ser Arg Pro Ser
            20                  25                  30

Pro Phe Asp Leu Phe Ile Arg Lys Ser Pro Thr Ile
        35                  40

<210> SEQ ID NO 39
<211> LENGTH: 56
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 39

Gln Lys His Trp Leu Ser Asp Arg Thr Tyr Thr Ser Gln Val Thr Tyr
1               5                   10                  15

Gln Gly His Thr Phe Glu Asp Ser Thr Lys Lys Cys Ala Asp Ser Asn
            20                  25                  30

Pro Arg Gly Val Ser Ala Tyr Leu Ser Arg Pro Ser Pro Phe Asp Leu
        35                  40                  45

Phe Ile Arg Lys Ser Pro Thr Ile
    50                  55

<210> SEQ ID NO 40
<211> LENGTH: 76
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as sourcee

<400> SEQUENCE: 40

Gln Lys His Trp Leu Ser Asp Arg Thr Tyr Thr Cys Gln Val Thr Tyr
1               5                   10                  15

Gln Gly His Thr Phe Glu Asp Ser Thr Lys Lys Cys Ala Asp Ser Asn
            20                  25                  30

Pro Arg Gly Val Ser Ala Tyr Leu Ser Arg Pro Ser Pro Phe Asp Leu
        35                  40                  45

Phe Ile Arg Lys Ser Pro Thr Ile Thr Cys Leu Val Val Asp Leu Ala
    50                  55                  60

Pro Ser Lys Gly Thr Val Asn Leu Thr Trp Ser Arg
65                  70                  75

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 41

Cys Lys Gln Arg Asn Gly Thr Leu Thr Cys
1               5                   10

<210> SEQ ID NO 42
<211> LENGTH: 45
<212> TYPE: PRT

<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 42

Gln Lys His Trp Leu Ser Asp Arg Thr Tyr Thr Cys Gln Val Thr Tyr
1               5                   10                  15

Gln Gly His Thr Phe Glu Asp Ser Thr Lys Cys Ala Asp Ser Asn
            20                  25                  30

Pro Arg Gly Val Ser Ala Tyr Leu Ser Arg Pro Ser Pro
        35                  40                  45

<210> SEQ ID NO 43
<211> LENGTH: 34
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 43

Cys Pro Ser Lys Gly Thr Val Asn Leu Thr Trp Ser Arg Ala Ser Gly
1               5                   10                  15

Lys Pro Val Asn His Ser Thr Arg Lys Glu Glu Lys Gln Arg Asn Gly
            20                  25                  30

Thr Cys

<210> SEQ ID NO 44
<211> LENGTH: 33
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 44

Cys Pro Val Gly Thr Arg Asp Trp Ile Glu Gly Glu Thr Tyr Gln Cys
1               5                   10                  15

Arg Val Thr His Pro His Leu Pro Arg Ala Leu Met Arg Ser Thr Thr
            20                  25                  30

Cys

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 45

Ser Thr Thr Lys Thr Ser Gly Pro Arg Ala Ala Pro Glu Val
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 46

```
Cys Trp Ser Arg Ala Ser Gly Lys Pro Val Cys Asn His Ser
  1               5                  10
```

```
<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 47
```

```
Cys Ser Arg Pro Ser Pro Phe Asp Leu Phe Ile Arg Lys Ser Pro Thr
  1               5                  10                  15

Ile Thr Cys
```

```
<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 48
```

```
Cys Val Gly Thr Arg Asp Trp Ile Glu Gly Glu Pro Cys
  1               5                  10
```

```
<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as sourcee

<400> SEQUENCE: 49
```

```
Cys Pro Pro Val Gly Thr Arg Asp Trp Ile Glu Gly Glu Pro Cys
  1               5                  10                  15
```

```
<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 50
```

```
Cys Lys Glu Glu Lys Gln Arg Asn Gly Thr Leu Thr Val Thr Ser Cys
  1               5                  10                  15
```

```
<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 51
```

```
Lys Glu Glu Lys Gln Arg Asn Gly
  1               5
```

```
<210> SEQ ID NO 52
<211> LENGTH: 11
```

```
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 52

Cys Trp Ser Arg Ala Ser Gly Lys Pro Val Cys
 1               5                  10

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 53

Pro Thr Ile Thr Cys Leu Val Leu Asp Leu Ala Pro Ser Lys Gly Thr
 1               5                  10                  15

Val Asn Leu Thr Cys
            20

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 54

Pro Thr Ile Thr Cys Leu Val Leu Asp Leu Ala Pro Ser Lys Gly Thr
 1               5                  10                  15

<210> SEQ ID NO 55
<211> LENGTH: 25
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 55

Thr Ser Thr Leu Pro Val Gly Thr Arg Asp Trp Ile Glu Gly Glu Thr
 1               5                  10                  15

Tyr Gln Cys Arg Val Thr His Pro His
            20                  25

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 56

Pro Thr Ile Thr Ser Leu Val Leu Cys Leu Ala Pro Ser Lys Gly Cys
 1               5                  10                  15

<210> SEQ ID NO 57
<211> LENGTH: 23
<212> TYPE: PRT
<213> ORGANISM: Artificial Sequence
<220> FEATURE:
```

-continued

<223> OTHER INFORMATION: Description of Artificial Sequence: Peptide
      synthesized from amino acids with no genetic material as source

<400> SEQUENCE: 57

Cys Val Asn Leu Thr Trp Ser Arg Ala Ser Gly Lys Pro Val Asn His
 1               5                  10                  15

Ser Thr Arg Lys Glu Glu Cys
            20

<210> SEQ ID NO 58
<211> LENGTH: 53
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 58

Cys Thr Trp Ser Arg Ala Ser Gly Lys Pro Val Asn His Ser Thr Arg
 1               5                  10                  15

Lys Glu Glu Lys Gln Arg Asn Gly Thr Leu Thr Val Thr Ser Thr Leu
            20                  25                  30

Pro Val Gly Thr Arg Asp Trp Ile Glu Gly Glu Thr Tyr Gln Cys Arg
        35                  40                  45

Val Thr His Pro His
        50

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 59

Lys Thr Lys Gly Ser Gly Phe Phe Val Phe
 1               5                  10

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: (4)
<223> OTHER INFORMATION: S, T
<221> NAME/KEY: MOD_RES
<222> LOCATION: (7)
<223> OTHER INFORMATION: K, R
<221> NAME/KEY: MOD_RES
<222> LOCATION: (8)
<223> OTHER INFORMATION: G, T
<221> NAME/KEY: MOD_RES
<222> LOCATION: (12)
<223> OTHER INFORMATION: H, T
<221> NAME/KEY: MOD_RES
<222> LOCATION: (13)
<223> OTHER INFORMATION: K, R
<221> NAME/KEY: MOD_RES
<222> LOCATION: (16)
<223> OTHER INFORMATION: G, T

<400> SEQUENCE: 60

Ile Ser Ile Xaa Glu Ile Xaa Xaa Val Ile Val Xaa Xaa Ile Glu Xaa
 1               5                  10                  15

Ile Leu Phe

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 61

Leu Ser Glu Ile Lys Gly Val Ile Val His Arg Leu Glu Gly Val
 1               5                  10                  15

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 62

Gly Ile Leu Glu Ser Arg Gly Ile Lys Ala Arg Ile Thr His Val Asp
 1               5                  10                  15

Thr Glu Ser Tyr
            20

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 63

Lys Lys Gln Tyr Ile Lys Ala Asn Ser Lys Phe Ile Gly Ile Thr Glu
 1               5                  10                  15

Leu

<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 64

Lys Lys Phe Asn Asn Phe Thr Val Ser Phe Trp Leu Arg Val Pro Lys
 1               5                  10                  15

Val Ser Ala Ser His Leu
            20

<210> SEQ ID NO 65
<211> LENGTH: 30
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 65

Lys Lys Leu Arg Arg Leu Leu Tyr Met Ile Tyr Met Ser Gly Leu Ala

```
              1               5              10              15
Val Arg Val His Val Ser Lys Glu Glu Gln Tyr Tyr Asp Tyr
                     20              25              30
```

<210> SEQ ID NO 66
<211> LENGTH: 27
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 66

```
Tyr Asp Pro Asn Tyr Leu Arg Thr Asp Ser Asp Lys Asp Arg Phe Leu
 1               5              10                      15
Gln Thr Met Val Lys Leu Phe Asn Arg Ile Lys
             20                  25
```

<210> SEQ ID NO 67
<211> LENGTH: 24
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 67

```
Gly Ala Tyr Ala Arg Cys Pro Asn Gly Thr Arg Ala Leu Thr Val Ala
 1               5                  10                  15
Glu Leu Arg Gly Asn Ala Glu Leu
             20
```

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 68

```
Phe Phe Leu Leu Thr Arg Ile Leu Thr Ile Pro Gln Ser Leu Asp
 1               5                  10                  15
```

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 69

```
Val Ser Phe Gly Val Trp Ile Arg Thr Pro Pro Ala Tyr Arg Pro Pro
 1               5                  10                  15
Asn Ala Pro Ile Leu
             20
```

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

```
<400> SEQUENCE: 70

Ser Asp Phe Phe Pro Ser Val Arg Asp Leu Leu Asp Thr Ala Ser Ala
 1               5                  10                  15

Leu Tyr Arg Glu
            20

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 71

Pro His His Thr Ala Leu Arg Gln Ala Ile Leu Cys Trp Gly Glu Leu
 1               5                  10                  15

Met Thr Leu Ala
            20

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 72

Trp Val Arg Asp Ile Ile Asp Asp Phe Thr Asn Glu Ser Ser Gln Lys
 1               5                  10                  15

Thr

<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 73

Arg Ala Gly Arg Ala Ile Leu His Ile Pro Thr Arg Ile Arg Gln Gly
 1               5                  10                  15

Leu Glu Arg

<210> SEQ ID NO 74
<211> LENGTH: 21
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 74

Ala Val Ala Glu Gly Thr Asp Arg Val Ile Glu Val Leu Gln Arg Ala
 1               5                  10                  15

Gly Arg Ala Ile Leu
            20

<210> SEQ ID NO 75
<211> LENGTH: 25
<212> TYPE: PRT
<213> ORGANISM: Artificial Sequence
```

```
<220> FEATURE:
<223> OTHER INFORMATION: Description of Artificial Sequence: Peptide
      synthesized from amino acids with no genetic material as source

<400> SEQUENCE: 75

Ala Leu Asn Ile Trp Asp Arg Phe Asp Val Phe Ser Thr Leu Gly Ala
 1               5                  10                  15

Thr Ser Gly Tyr Leu Lys Gly Asn Ser
            20                  25

<210> SEQ ID NO 76
<211> LENGTH: 22
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 76

Asp Ser Glu Thr Ala Asp Asn Leu Glu Lys Thr Val Ala Ala Leu Ser
 1               5                  10                  15

Ile Leu Pro Gly His Gly
            20

<210> SEQ ID NO 77
<211> LENGTH: 39
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 77

Glu Glu Ile Val Ala Gln Ser Ile Ala Leu Ser Ser Leu Met Val Ala
 1               5                  10                  15

Gln Ala Ile Pro Leu Val Gly Glu Leu Val Asp Ile Gly Phe Ala Ala
            20                  25                  30

Thr Asn Phe Val Glu Ser Cys
        35

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 78

Asp Ile Glu Lys Lys Ile Ala Lys Met Glu Lys Ala Ser Ser Val Phe
 1               5                  10                  15

Asn Val Val Asn Ser
            20

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 79

Lys Trp Phe Lys Thr Asn Ala Pro Asn Gly Val Asp Glu Lys Ile Arg
 1               5                  10                  15
```

Ile

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 80

Gly Leu Gln Gly Lys Ile Ala Asp Ala Val Lys Ala Lys Gly
 1               5                  10

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 81

Gly Leu Ala Ala Gly Leu Val Gly Met Ala Ala Asp Ala Met Val Glu
 1               5                  10                  15

Asp Val Asn

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 82

Ser Thr Glu Thr Gly Asn Gln His His Tyr Gln Thr Arg Val Val Ser
 1               5                  10                  15

Asn Ala Asn Lys
            20

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 83

Cys Pro Ser Pro Phe Asp Leu Phe Ile Arg Lys Ser Pro Thr Cys
 1               5                  10                  15

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 84

Cys Gly Glu Thr Tyr Lys Ser Thr Val Ser His Pro Asp Leu Pro Arg
 1               5                  10                  15

Glu Val Val Arg Ser Ile Ala Lys Cys

-continued

```
              20                  25

<210> SEQ ID NO 85
<211> LENGTH: 60
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source
<221> NAME/KEY: MOD_RES
<222> LOCATION: (18)
<223> OTHER INFORMATION: S, T
<221> NAME/KEY: MOD_RES
<222> LOCATION: (21)
<223> OTHER INFORMATION: K, R
<221> NAME/KEY: MOD_RES
<222> LOCATION: (22)
<223> OTHER INFORMATION: G, T
<221> NAME/KEY: MOD_RES
<222> LOCATION: (26)
<223> OTHER INFORMATION: H, T
<221> NAME/KEY: MOD_RES
<222> LOCATION: (27)
<223> OTHER INFORMATION: K, R
<221> NAME/KEY: MOD_RES
<222> LOCATION: (30)
<223> OTHER INFORMATION: G, T

<400> SEQUENCE: 85

Thr Ile Asn Lys Pro Lys Gly Tyr Val Gly Lys Glu Gly Gly Ile Ser
 1               5                  10                  15

Ile Xaa Glu Ile Xaa Xaa Val Ile Val Xaa Xaa Ile Glu Xaa Ile Leu
             20                  25                  30

Phe Gly Gly Cys Gly Gly Thr Tyr Gln Ser Arg Val Thr His Pro His
         35                  40                  45

Leu Pro Arg Ala Leu Met Arg Ser Thr Thr Lys Cys
     50                  55                  60

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 86

Lys Trp Phe Lys Thr Asn Ala Pro Asn Gly Val Asp Glu Lys Ile Arg
 1               5                  10                  15

Ile

<210> SEQ ID NO 87
<211> LENGTH: 62
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 87

Lys Trp Phe Lys Thr Asn Ala Pro Asn Gly Val Asp Glu Lys Ile Arg
 1               5                  10                  15

Ile Lys Lys Lys Lys Ile Ile Thr Ile Thr Arg Ile Ile Thr Ile Ile
             20                  25                  30

Thr Thr Ile Asp Lys Cys Gly Glu Thr Tyr Tyr Ser Arg Val Thr His
         35                  40                  45
```

-continued

```
Pro His Leu Pro Lys Asp Ile Val Arg Ser Ile Ala Lys Cys
        50                  55                  60

<210> SEQ ID NO 88
<211> LENGTH: 57
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 88

Thr Ile Asn Lys Pro Lys Gly Tyr Val Gly Lys Glu Lys Lys Lys
  1               5                  10                  15

Ile Ile Thr Ile Thr Arg Ile Ile Thr Ile Ile Thr Tyr Ile Asp Lys
             20                  25                  30

Cys Gly Glu Thr Tyr Tyr Ser Arg Val Thr His Pro His Leu Pro Lys
             35                  40                  45

Asp Ile Val Arg Ser Ile Ala Lys Cys
        50                  55

<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 89

Ile Ser Leu Thr Glu Ile Arg Thr Val Ile Val Thr Arg Leu Glu Thr
  1               5                  10                  15

Val Leu Phe

<210> SEQ ID NO 90
<211> LENGTH: 45
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 90

Ile Ser Leu Thr Glu Ile Arg Thr Val Ile Val Thr Arg Leu Glu Thr
  1               5                  10                  15

Val Leu Phe Lys Cys Gly Glu Thr Tyr Tyr Ser Arg Val Thr His Pro
             20                  25                  30

His Leu Pro Lys Asp Ile Val Arg Ser Ile Ala Lys Cys
             35                  40                  45

<210> SEQ ID NO 91
<211> LENGTH: 63
<212> TYPE: PRT
<213> ORGANISM: Artificial Sequence
<220> FEATURE:
<223> OTHER INFORMATION: Description of Artificial Sequence: Peptide
      synthesized from amino acids with no genetic material as source

<400> SEQUENCE: 91

Lys Trp Phe Lys Thr Asn Ala Pro Asn Gly Val Asp Glu Lys Ile Arg
  1               5                  10                  15

Ile Lys Ile Ser Leu Thr Glu Ile Arg Thr Val Ile Val Thr Arg Leu
             20                  25                  30
```

-continued

```
Glu Thr Val Leu Phe Lys Cys Gly Glu Thr Tyr Tyr Ser Arg Val Thr
            35                  40                  45

His Pro His Leu Pro Lys Asp Ile Val Arg Ser Ile Ala Lys Cys
        50                  55                  60
```

PEPTIDE COMPOSITION AS IMMUNOGEN FOR THE TREATMENT OF ALLERGY

CROSS REFERENCE TO RELATED APPLICATIONS

The present application is the national phase of PCT application No. PCT/US99/13959, filed Jun. 21, 1999, which is a continuation-in-part application of U.S. application Ser. No. 09/100,287 filed Jun. 20, 1998 now abandoned.

FIELD OF THE INVENTION

The present invention relates to the use of peptide conjugate compositions as an immunogen, with each peptide conjugate contained therein comprising a target antigenic site on the third constant domain (CH3) of the to epsilon (ε) heavy chain of IgE, with said target antigenic site covalently linked to (1) a carrier protein through chemical coupling, or (2) a helper T cell epitope and other immunostimulatory sequences through chemical coupling or through direct synthesis, for the treatment of allergy.

More particularly, the present invention relates to the use of such peptide conjugate compositions as an immunogen to elicit the production, in mammals including humans, of high titer polyclonal antibodies specific to a target effector site on the CH3 domain of the ε heavy chain of IgE, and to the use of such composition as a pharmaceutical to provide an immunotherapy for IgE-mediated allergic diseases.

BACKGROUND OF THE INVENTION

In the immune system of humans and other mammals, IgE mediates type I hypersensitivities. These are the allergic responses to certain foods, drugs, and environmental allergens which are manifested by such symptoms as allergic rhinitis, asthma, allergic dermatitis, and anaphylaxis. Existing strategies to treat allergic diseases are of limited utility, consisting of attempts to either desensitize the atopic individual to an identified allergen or to ameliorate an ongoing allergic reaction with therapeutic compounds. Limitations to allergen-based desensitization immunotherapy include difficulties in identifying the allergen involved and the adverse reactions frequently caused by the use of the identified allergen (World Health Organization and International Union of Immunological Societies Working Group, *Lancet*, 1989; i:259–261). Other treatments for the relief of allergies employ therapeutic compounds to block the acute inflammatory cascade that is responsible for allergic reactions. These compounds include anti-histamines, decongestants, $\beta_2$ agonists, and corticosteroids. Anti-histamines, decongestants, and $\beta_2$ agonists act on events downstream of IgE in the allergic cascade, making them palliative remedies which address allergic symptoms rather than preventative treatments which must act on events closer to the initiation of IgE-mediated allergic reactions. These palliative remedies provide relief that is short term and partial, frequently accompanied by adverse side effects. Many patients with severe allergies are effectively treated with corticosteroids. Steroid therapy reduces inflammation but is broadly immunosuppressive.

To avoid the shortcomings of the known therapeutic drugs, it would be more desirable to prevent allergic responses by selective intervention targeted to IgE. In common with the other immunoglobulins, IgE has two heavy chains and two light chains. The ε heavy chain has five domains, a variable VH domain and constant domains CH1 to CH4. The constant domains from both ε chains of an IgE molecule combine to comprise the constant or Fc region of IgE. IgE circulates and becomes attached to effector cells such as basophils and mast cells through a site on the IgE Fc region, becoming bound to a high affinity FcεRI receptor on the cell surface. In an allergic response, allergens (e.g., pollen, dust mite proteins, flea antigens) bind to the antigen-binding sites on the variable region of mast cell or basophil-bound IgE. This action crosslinks the IgE molecules and the underlying FcεRI receptors. The IgE-allergen complexes thereby signal the degranulation of mast cells and basophils with the concomitant release of histamine and the other inflammatory mediators. These mediators produce the symptoms of allergy, up-regulate the production of IgE, and result in heightened sensitivity to the allergen (Davis et al., *Springer Semin Immunopathol*, 1993; 15: 51–73).

It has been suggested that allergic diseases may be treated by interventions which inhibit the binding of IgE to mast cells and basophils. For example, synthetic peptides corresponding to various sites on the Fc of IgE have been studied as competitive inhibitors for the binding of IgE to the FcεRI receptor, The presumption of the investigators has been that such peptides act as antagonists for sites on IgE that participate in the binding of IgE to the FcεRI receptor, and serve to map portions of the binding site.

The amino acid residues of the competitively inhibiting IgE peptides and of all IgE peptides to follow, including non-human IgE peptide homologues, are indexed in accordance with the numbering for human IgE given by Dorrington and Bennich, (*Immunol Rev*, 1978; 41: 3–25, also accessible at internet location http://www.pdb.bnl.gov/pdb.bin/pdbids). That human sequence is listed here as SEQ ID NO:1 and is numbered as shown in Table 1. The homologous dog, rat and mouse sequences for IgE (Patel et al., *Immunogenetics*, 1995; 41: 282–286; Steen et al., *J Mol Biol*, 1984; 177: 19–32; and, Ishida et al., *EMBO*, 1982; 1: 1117–1123) are also shown in Table 1 and listed as SEQ ID NOS: 2, 3, and 4 respectively. The animal sequences are shown in register with human IgE. Individual amino acid positions in human IgE, and in homologues from other species, are identified herein according to the numbering system for the amino acid sequences shown in Table 1, unless otherwise specified.

Helm et al. (*Nature*, 1988; 331:180–183) have shown that a 76 amino acid long recombinant polypeptide, spanning the C-terminal CH2 and N-terminal CH3 region of human IgE, from amino acids 301–376, reduces binding of IgE to human mast cells by competitive inhibition. Other studies reported that only the CH3 domain is involved with binding to FcεRI. For example, a rat sequence peptide corresponding to amino acids 401–415 of the human sequence (Table 1) inhibited the binding of rat IgE to rat mast cells (Burt and Stanworth, *Eur J Immunol*, 1987; 17:437–440). A peptide of residues 419 to 463 from human IgE prevented the sensitization of rat mast cells (Nio et al., *FEBS Lett*, 1992; 314: 229–231). Jardieu and Presta (WO 93/04173) reported on peptides homologous to the CH3 and CH4 regions which may include amino acids 373–390, 420–428, 446–453, and adjacent regions, which differentially bind to the FcεRI receptor. However, high concentrations of all such peptides were required to achieve effective inhibition of IgE binding. These high concentrations are predictive of excessively large doses for significant physiological effect, and are not therapeutically practical.

Anti-IgE antibodies have also been applied as a method for mapping sites on IgE that participate in binding to the FcεRI receptor. Studies with mouse monoclonal antibodies directed against various domains of IgE Fc revealed that anti-IgE monoclonal antibodies with specificities for the CH3 domain inhibit the binding of IgE to its high affinity receptor (Baniyash et al., *Molec Immunol*, 1988; 25: 705–711; and, Stadler et al., *Immunol Cell Biol*, 1996; 74: 195–200). These monoclonal antibody studies are in agreement with earlier studies that used polyclonal antipeptide antibodies to map sites that are apparently involved in receptor binding. For example, rabbit antibodies with specificities for IgE amino acid positions 401–415 (Burt et al., *Molec Immunol*, 1987; 24: 379–389), and 355–368 (Robertson and Liu, *Molec Immunol*, 1988; 25:103–113) showed specificity for unbound IgE but reacted poorly with receptor-bound IgE.

A canine IgE peptide fragment containing at least five continuous amino acids from dog IgE amino acids 356–479 is useful for the preparation of antibodies for diagnosis of allergy in dogs (JP 9179795, 1997). Those results are suggestive of surface-exposed effector sites in the CH3 domain of the dog ε chain, but no such effector site is taught nor is a therapeutic application disclosed for the anti-IgE antibodies.

These epitope mapping studies demonstrate most consistently that the CH3 domain of the ε heavy chain can be targeted for interventions aimed at inhibiting the binding of IgE to basophils and mast cells. However, the various studies are quite inconsistent on precise locations for sites on CH3 that are most useful. Also, results from cross-inhibition studies on IgE, with site-specific antibodies (e.g., Burt et al., 1987) have frequently been over-interpreted to signify that they have defined a precise location for the FcεR1 binding site on the ε chain. Interpretation of such cross-inhibition studies is limited because it cannot be assumed that an antibody recognition site is equivalent to a ligand binding site. Antibodies may inhibit by directly binding to the desired target site, but they can also occupy non-continuous effector sites and inhibit ligand binding through steric hindrance or induction of conformational change.

Therefore, the epitope mapping studies have provided empirical observations but have not resolved the binding site for the high affinity receptor within the CH3 domain. In the absence of a defined binding site, no means is available for the reliable prediction of potentially therapeutic synthetic immunogens with immunologic crossreactivities for effector sites that participate directly or indirectly in binding to FcεR1.

Furthermore, in the absence of X-ray crystallography data for IgE, the available structural models for IgE are not sufficient for the reliable prediction of the sites on IgE that are suitable for anti-IgE interventions. Conflicting structures based on the divulged three-dimensional structure of IgG have been modeled for IgE and for the CH2/CH3 region of IgE that is associated with the interaction between IgE and its high affinity receptor. These models propose various conformationally dependent structures for the site, involving contact with linearly non-adjacent residues of the IgE molecule. Some models for the site suggest interactions between non-contiguous sites on the same ε chain mediated by intramolecular disulfide bonded loops (Helm et al., *Eur J Immunol*, 1991; 21:1543–1548) or intramolecular loops maintained by electrostatic interactions (Presta et al., *J Biol Chem*, 1994; 269: 26368–26373). Other models propose intermolecular interactions between segments of the dimerized ε chains of an IgE molecule (McDonnell et al., *Biochem Soc Trans*, 1997; 25: 387–392). In fact, experimental observations show that potential contact points comprise several scattered and discontinuous sites on the CH3 domain of the ε chain and make it clear that the three-dimensional structure of the FcεR1 binding site cannot be readily resolved by modeling (Helm et al., 1988; Baniyash et al., 1988; and, Presta et al., 1994). Therefore, the identification of useful synthetic peptide antagonists and immunogens that mimic effector sites on IgE has not been disclosed by theoretical modeling. In the absence of a structure for IgE resolved by X-ray crystallography, such useful peptide sites can only be arrived at by empirical experimentation.

The concept of treating allergic diseases with anti-IgE antibodies, of specificities that inhibit the binding of IgE to the high affinity receptor on basophils and mast cells, also has been known (Stadler et al., 1996; Davis et al., 1993). Such anti-IgE antibodies are either anaphylactogenic (crosslinking) or non-anaphylactogenic (non-crosslinking). Most such anti-IgE antibodies are anaphylactogenic. They will bind and crosslink IgE on the surface of basophils and mast cells and trigger the release of the pharmacologic mediators of allergy. This crosslinking-could lead to anaphylaxis and death.

It is therefore crucial that anti-IgE antibodies for treatment be non-anaphylactogenic. Certain non-anaphylactogenic antibodies retain specificity for the CH3 domain of the c chain and do not crosslink cell-bound IgE, while displaying inhibitory activity for IgE-mediated histamine release (Davis et al., 1993; Stadler et al., 1996). Rup and Kahn (U.S. Pat. No. 4,940,782) report such a non-anaphylactogenic monoclonal antibody that reacts with free rat IgE and rat IgE bound to B cells, but not IgE bound to the rat mast cell FcεR1 receptor. Most significantly, it inhibits the sensitization of rat mast cells. The non-anaphylactogenic antibodies with homologous specificities for human IgE also inhibit sensitization by the same action mode. These anti-human IgE antibodies bind free serum IgE, bind to B cell-bound IgE, fail to bind to IgE attached to the basophil and mast cell high affinity receptor and prevent sensitization of human cells. These antibodies are presumed to act by specificity for the site on IgE that binds to the FcεR1 receptor (Rup and Kahn, U.S. Pat. No. 4,940,782; Davis et al., 1993; Chang, U.S. Pat. No. 5,420,251; Presta et al., *J Immunol*, 1993; 151: 2623–2632). In addition, a non-anaphylactogenic anti-human IgE monoclonal antibody with a different specificity has been found that also neutralizes free IgE (Rudolf et al., *J Immunol*, 1996; 157: 5646–5652). This anti-IgE does not directly bind with the receptor binding site because it also recognizes FcεR1-bound IgE. Apparently, it functions to reduce sensitization of basophils by altering the thermodynamic balance of receptor-bound versus free IgE.

Thus, anti-IgE antibodies that directly bind to the FcεR1 binding site and anti-IgE antibodies that interfere with FcεR1 binding at other effector sites, both serve to block the sensitization of mast cells and basophils by free IgE. These potentially immunotherapeutic antibodies identify CH3 as the domain of IgE that interacts with the high affinity IgE Fc receptor, in agreement with the previous mapping studies. However, a more precise identification of the binding site and alternative useful effector sites such as that described by Rudolf et al. remain elusive. Rudolf et al. have also used a phage display library to identify mimotope peptides which bind to their anti-IgE monoclonal antibody; however, the peptide mimotopes did not show homology to the primary amino acid sequence of human IgE (Rudolf et al., *J. Immunol.*, 1998; 160: 3315–3321).

A humanized monoclonal anti-IgE antibody with apparent specificity for the FcεR1 receptor site is under clinical study in humans for the treatment of allergy by passive immunotherapy (MacGlashan et al., *J Immunol*, 1997; 158:1438–1445). It has been found that infusion with that antibody, rhuMAb-E25, reduces the serum concentration of IgE in patients, down-regulates the expression of IgE receptor on effector cells, reduces allergic sensitivities to challenge by allergen, and improves the symptoms of asthma and allergic rhinitis. The antibody displays a good safety profile. The clinical trial results establish the feasibility of an anti-IgE approach for the treatment of allergic diseases. But this treatment mode is problematical: Immunotherapy by the anti-IgE invention is accomplished by passive immunization, i.e., by infusion of the antibody. The antibody must be delivered in doses high enough and at frequencies often enough, via inconvenient intravenous or subcutaneous routes, to achieve a continuous pharmacologically effective concentration of antibody. The effective dose is determined by patient body weight, baseline level of free IgE in circulation, and by route of administration. In recent clinical trials, the steady-state concentration required for therapeutic efficacy was achieved by two weekly doses and maintained thereafter by biweekly doses. A full course of treatment for a typical allergy patient would expend a total of 2000–3000 mg of humanized antibody and requires seven to 10 inconvenient intravenous administrations (MacGlashan et al., 1997; Boulet et al., Am J Respir Crit Care Med, 1997; 155:1835–1840). The cost for this amount of antibody and the expense and inconvenience of multiple infusions in a hospital setting suggest that this treatment is too expensive for all but a small proportion of the patient population.

The clinical effectiveness of the monoclonal antibody rhuMAb-E25 establishes the feasibility of immunotherapy by passively administered anti-IgE. It also provides the rationale for an alternative anti-IgE approach by active immunization, if and when such immunogens can be designed.

An anti-IgE treatment affected by active immunization with an IgE immunogen, i.e., by "vaccination" against endogenous IgE, would be preferable on the basis of cost and convenience. "Vaccination" against IgE offers advantages over passive immunization: small amounts of inexpensive immunogen, infrequent and conveniently administered intramuscular injections, and no need to customize murine antibodies for compatibility with the subject species, i.e., to "humanize" antibodies for use in humans, since the procedure uses the patient's own immune system to produce antibodies. However, while the desensitizing monoclonal antibodies cited above may be suggestive of the desirability of IgE immunogens, they do not disclose the identity of safe and effective immunogens. Such immunogens must mimic relevant IgE effector sites with fidelity sufficient to evoke cross-inhibitory antibodies, while retaining site-specificity sufficient to avoid induction of anaphylactogenic antibodies. Moreover, effective IgE immunogens must be highly immunostimulatory. There remains a need for such immunogens, of relevant and safe site-specificity, and of sufficient immunopotency.

IgE immunogens for immunotherapy of allergy must be immunostimulatory so as to evoke levels of anti-IgE sufficient to reduce IgE-mediated sensitization. Such immunogens must be designed to overcome the strong tolerance exhibited towards self molecules. Haba and Nisonoff (Proc Natl Acad Sci USA, 1990; 87:3363–3367) induced an effective anti-IgE response in mice only by immunizations with IgE during a short neonatal window of development, from birth to day 10. Vaccinations initiated beyond this time failed to induce the desired autoimmune response unless the IgE used to immunize the mice had been covalently coupled to a foreign carrier protein, keyhole limpet hemocyanin (KLH). Similarly, a desensitizing anti-IgE response was evoked in rats by a recombinant protein comprising the CH2–CH3 ε chain domains fused to the glutathione-S-transferase protein of Schistosoma japonicum (Hellman, Eur J Immunol, 1994; 24:415–420).

Other investigators have been concerned with minimizing the risk of evoking anaphylactogenic anti-IgE antibodies that crosslink IgE already bound to the surface of mast cells and basophils by seeking peptide IgE immunogens of finer site specificity. For example, a peptide corresponding to a site in the CH4 domain of IgE (residues 497–506 of SEQ ID NO:1) was coupled to KLH and used to induce polyclonal antibodies that were effective in suppressing IgE-mediated signal transduction in rat mast cells. However, the peptide-KLH conjugate displayed poor immunostimulatory capabilities which necessitated demonstration of efficacy by passive immunization of rats with peak immune rabbit antiserum (Stanworth et al., Lancet, 1990; 336:1279–1281). The CH4 immunogen of Stanworth et al. was later produced, by the work of the present inventor, as a series of wholly synthetic immunogens by synthesis that provided covalent linkage to promiscuous human T helper epitopes. Immunogenicity of these peptides was improved over that of the original KLH-peptide conjugate, but no evidence was provided for the efficacy of resultant anti-IgE CH4 antibodies (Wang, WO 95/26365). Furthermore, as shown herein in Example 1 (Table 2, entry 34), anti-peptide antibodies with specificity for the previously disclosed CH4 effector site (Stanworth et al., 1990) had no crossreactivity to human IgE. The earlier antipeptide studies of Burt and Stanworth (1987) targeted to the IgE-CH3 401–415 peptide also provided evidence of evoking desensitizing cross-reactivity, but this too required selected peak rabbit antiserum and use of an ill-defined peptide-carrier protein conjugate to observe effects by passive immunization in a rat model. No synthetic peptides have ever been demonstrated to be effective in eliciting the production in immunized hosts of polyclonal antisera capable of inhibition of histamine release.

The improvement of the prior art immunogens discussed above is necessary before a synthetic peptide immunogen of immunogenicity and specificity sufficient for efficacy and safety can be attained. The present invention accomplishes these improvements through incorporation of a collection of additional methods for the identification and design of synthetic peptide immunogens. These methods include: (1) an effective procedure for the identification of an effective target epitope; (2) the means to augment the immunogenicity of a B cell target epitope by combining it with a peptide comprising broadly reactive promiscuous T helper cell (Th) epitope; (3) the means of enlarging the repertoire of T cell epitopes by application of combinatorial peptide chemistry and thereby further accommodate the variable immune responsiveness of an outbred population; and (4) the stabilization of conformational features by the introduction of cyclic constraints, so as to maximize cross-reactivity to the native molecule.

Synthetic peptides have been used for "epitope mapping" to identify immunodominant determinants or epitopes on the surface of proteins, for the development of new vaccines and diagnostics. Epitope mapping employs a series of overlapping peptides corresponding to regions on the protein of interest to identify sites which participate in antibody-immunogen determinant interaction. Most commonly, epitope mapping employs peptides of relatively short length to precisely detect linear determinants. A fast method of epitope mapping known under the trademark "PEPSCAN" is based on the simultaneous synthesis of hundreds of overlapping peptides, of lengths of 8 to 14 amino acids, coupled to solid supports. The coupled peptides are tested for their ability to bind antibodies. The PEPSCAN approach is effective in localizing linear determinants, but not for the identification of epitopes needed for mimicry of discontinuous effector sites such as the FcεR1 binding site (Meloen et al., Ann Biol Clin, 1991; 49:231–242). An alternative method relies on a set of nested and overlapping peptides of multiple lengths ranging from 15 to 60 residues. These longer peptides can be reliably synthesized by a laborious series of independent solid-phase peptide syntheses, rather than by the rapid and simultaneous PEPSCAN syntheses. The resulting set of long nested and overlapping peptides can then be used for analyses of antibody binding in systems such as experimental immunizations and natural infections, to identify long peptides which best present immunodominant determinants, including simple discontinuous epitopes. This method is exemplified by the studies of Wang for the mapping of immunodominant sites from HTLV I/II (U.S. Pat. No. 5,476,765) and HCV (U.S. Pat. No. 5,106,726); and it was used for the selection of a precise position on the gp120 sequence for optimum presentation of an HIV neutralizing epitope (Wang et al., Science, 1991; 254:285–288).

Peptide immunogens are generally more flexible than proteins and tend not to retain any preferred structure. Therefore it is useful to stabilize a peptide immunogen by the introduction of cyclic constraints. A correctly cyclized peptide immunogen can mimic and preserve the conformation of a targeted epitope and thereby evoke antibodies with cross-reactivities for that site on the authentic molecule (Moore, Chapter 2 in *Synthetic Peptides: A User's Guide*, ed Grant, WH Freeman and Company: New York, 1992, pp 63–67).

Another important factor affecting the immunogenicity of an IgE-derived peptide for an allergy pharmaceutical is its presentation to the immune system by T helper cell epitopes that react with a host's T-helper cell receptors and Class II MHC molecules (Babbitt et al., Nature, 1985; 317: 359–361). These are often provided by carrier proteins with concomitant disadvantages due to the difficulties for the manufacture of well-defined peptide-carrier conjugates, misdirection of most antibody response to the carrier, and carrier-induced epitopic suppression (Cease, *Intern Rev Immunol.*, 1990; 7: 85–107; Schutze et al., *J Immunol.*, 1985; 135: 2319–2322). Alternatively, T-helper cell epitopes (Th) may also be supplied by synthetic peptides comprising Th sites. Thus, Th epitopes termed promiscuous Th evoke efficient T cell help and can be combined with synthetic B cell epitopes that by themselves are poorly immunogenic to generate potent peptide immunogens (U.S. Pat. No. 5,759,551). Well-designed promiscuous Th/B cell epitope chimeric peptides are capable of eliciting Th responses and resultant antibody responses in most members of a genetically diverse population expressing diverse MHC haplotypes. Promiscuous Th can be provided by specific sequences derived from potent foreign antigens, such as for example measles virus F protein, hepatitis B virus surface antigen, and *Chlamydia trachomatis* major outer membrane protein (MOMP). Many known promiscuous Th, taken from viral and bacterial pathogens, have been shown to be effective in potentiating a poorly immunogenic peptide corresponding to the decapeptide hormone LHRH (U.S. Pat. No. 5,759,551)

Promiscuous Th epitopes derived from foreign pathogens may include, but are not limited to, hepatitis B surface and core antigen helper T cell epitopes ($HB_s$ Th and $HB_c$ Th), pertussis toxin helper T cell epitopes (PT Th), tetanus toxin helper T cell epitopes (TT Th), measles virus F protein helper T cell epitopes ($MV_F$ Th), *Chlamydia trachomatis* major outer membrane protein helper T cell epitopes (CT Th), diphtheria toxin helper T cell epitopes (DT Th), *Plasmodium falciparum* circumsporozoite helper T cell epitopes (PF Th), *Schistosoma mansoni* triose phosphate isomerase helper T cell epitopes (SM Th), and *Escherichia coli* TraT helper T cell epitopes (TraT Th). The pathogen-derived Th were listed as SEQ ID NOS:2–9 and 42–52 in U.S. Pat. No. 5,759,551; as Chlamydia helper site P11 in Stagg et al., *Immunology*, 1993; 79;1–9; and as HBc peptide 50–69 in Ferrari et al., *J Clin Invest*, 1991; 88: 214–222.

Promiscuous Th epitopes range in size from about 15 to about 50 amino acid residues in length (U.S. Pat. No. 5,759,551) and often share common structural features and may contain specific landmark sequences. For example, a common feature is amphipathic helices, which are alpha-helical structures with hydrophobic amino acid residues dominating one face of the helix and with charged and polar resides dominating the surrounding faces (Cease et al., *Proc Natl Acad Sci USA*, 1987; 84:4249–4253). Th epitopes frequently contain additional primary amino acid patterns such as a Gly or charged residue followed by two to three hydrophobic residues, followed in turn by a charged or polar residue. This pattern defines what are called Rothbard sequences. Also, Th epitopes often obey the 1, 4, 5, 8 rule, where a positively charged residue is followed by hydrophobic residues at the fourth, fifth and eighth positions after the charged residue, consistent with an amphipathic helix having positions 1, 4, 5 and 8 located on the same face. Since all of these structures are composed of common hydrophobic, charged and polar amino acids, each structure can exist simultaneously within a single Th epitope (Partidos et al., *J Gen Virol*, 1991; 72:1293–1299). Most, if not all, of the promiscuous T cell epitopes fit at least one of the periodicities described above. These features may be incorporated into the designs of "idealized artificial Th sites".

Useful Th sites may also include combinatorial Th that incorporate selected degenerate sites into the design of the idealized Th sites. In Wang et al. (WO 95/11998), a particular class of a combinatorial epitope was designated as a "Structured Synthetic Antigen Library" or SSAL. A Th constructed as an. SSAL epitope is composed of positional substitutions organized around a structural framework of invariant residues. The sequence of the SSAL is determined by aligning the primary amino acid sequence of a promiscuous Th, retaining relatively invariant residues at positions responsible for the unique structure of the Th peptide and providing degeneracy at the positions associated with recognition of the diverse MHC restriction elements. Lists of variable and preferred amino acids are available for MHC-binding motifs (Meister et al., *Vaccine*, 1995; 13: 581–591: Alexander et al., *Immunity*, 1994, 1:751–761).

All members of the SSAL are produced simultaneously in a single solid-phase peptide synthesis in tandem with the targeted B cell epitope and other sequences. The Th library sequence maintains the binding motifs of a promiscuous Th and accommodates reactivity to a wider range of haplotypes. For example, the degenerate Th epitope described in WO 95/11998 as "SSAL1TH1" was modeled after a promiscuous epitope taken from the F protein of measles virus (Partidos et al., 1991). SSAL1TH1 was designed to be used in tandem with an LHRH target peptide. Like the measles epitope, SSAL1TH1 follows the Rothbard sequence and the 1, 4, 5, 8 rule:

```
 1              5                10                15
Asp-Leu-Ser-Asp-Leu-Lys-Gly-Leu-Leu-Leu-His-Lys-Leu-Asp-Gly-Leu
Glu Ile     Glu Ile Arg     Ile Ile Ile     Arg Ile Glu     Ile
    Val         Val         Val Val Val         Val         Val
    Phe         Phe         Phe Phe Phe         Phe         Phe
```

Charged residues Glu or Asp are added at position 1 to increase the charge surrounding the hydrophobic face of the Th. The hydrophobic face of the amphipathic helix is then maintained by hydrophobic residues at 2, 5, 8, 9, 10, 13 and 16, with variability at 2, 5, 8, 9, 10, 13, and 16 to provide a facade with the capability of binding to a wide range of MHC restriction elements. The net effect of the SSAL feature is to enlarge the range of immune responsiveness to an artificial Th (WO 95/11998).

Peptide immunogens that have been designed with the peptide technologies and peptide design elements discussed above, i.e., precise epitope mapping, cyclic constraint, and the incorporation of promiscuous Th epitopes or idealized promiscuous Th, and idealized SSAL Th epitopes, are the basis for the effective synthetic peptide IgE immunogens of the present invention. Such peptides are preferred for appropriate targeting and safety due to effective presentation of the IgE effector site by optimized positioning and cyclization, and for immunopotency due to broadly reactive Th responsiveness.

SUMMARY OF THE INVENTION

The present invention provides new synthetic peptide conjugate compositions for the treatment of IgE-mediated allergic diseases by active immunization. The immunization induces the production of high titer non-anaphylactogenic polyclonal antibodies specific to an effector site of IgE in an immunized host. This in turn prevents the triggering and activation of mast cells/basophils and down-regulates IgE synthesis.

Treatment is effected by immunization of the host with the peptide composition, with each peptide contained therein comprising a target antigenic peptide sequence (referred to herein as an "IgE-CH3 domain antigen" or "IgE-CH3 domain antigen-peptide") modified from a segment of the CH3 domain of the epsilon ($\epsilon$) heavy chain of human IgE (e.g., amino acids 413–435 of SEQ ID No:1 or SEQ ID NO:5) or the homologous sequence from other species (e.g. SEQ ID NOS:6–8 and 84).

In general, the IgE-CH3 domain antigen is a peptide sequence between about 25 and about 29 amino acids in length, is substantially homologous to the above segment of the CH3 domain of the epsilon heavy chain of a mammalian IgE antibody, and contains two cysteine residues separated by about 23 amino acid residues. In the present context, substantially homologous means that in addition to the two cysteine residues, which may be introduced by insertion or substitution, up to about four other amino acid substitutions (preferably conservative substitutions) may also be made.

Preferably, the target site is modified from that of the naturally occurring IgE sequences as follows:

(1) by the insertion of a cysteine residue to the N-terminus side of position 413 or homologous position, unless cysteine is already present at positions 413 or 414 in the natural sequence;

(2) by the conservative substitution (preferably of serine) for any native cysteines from positions 415 to 434 of the natural target sequence;

(3) by the insertion of cysteine at the C-terminus side of position 435 or homologous position unless cysteine is already present at positions 435 or 436 in the natural sequence; and (4) by the formation of a disulfide bond between the retained cysteines so as to produce a cyclic structure. The structures may also comprise 1 to 5 additional amino acids taken from either terminus of the 413–435 segment of IgE, provided that the single disulfide looped structure is preserved.

An optimized IgE-CH3 domain antigen peptide for human IgE, having the sequence Cys-Gly-Glu-Thr-Tyr-Gln-Ser-Arg-Val-Thr-His-Pro-His-Leu-Pro-Arg-Ala-Leu-Met-Arg-Ser-Thr-Thr-Lys-Cys (SEQ ID NO:5) is provided by the present invention. The human IgE target site is cyclized through the unnatural terminal cysteines and a serine residue substitutes for the cysteine residue of the natural sequence. Antibody that is evoked by peptide immunogens comprising this IgE-CH3 domain antigen is crossreactive with human IgE and inhibits the sensitization of human basophils by human IgE.

Likewise, corresponding target sites for IgE of other species can be derived from the homologous $\epsilon$ chain segment of the relevant species. For example, such target sequences can be taken from the dog, rat and mouse $\epsilon$ sequences shown in Table 1 (SEQ ID NOS: 2, 3 and 4), or the horse IgE-CH3 sequence provided by Navarro et al., *Molec. Immunol.*, 1995, 32:1–8. Additional IgE-CH3 domain antigen peptides (SEQ ID NOS: 6, 7, B, and 84), may be derived from these sequences.

Preferably, the IgE-CH3 domain antigens of the invention are rendered more immunogenic via covalent linkage to a carrier protein through chemical coupling, or more preferably via covalent linkage to synthetic immunostimulatory elements, such as promiscuous Th epitopes, through direct synthesis. Specific examples of carrier protein and immunostimulatory elements are provided, e.g., Keyhole Limpet Hemocyanin (KLH) carrier, an artificial Th (SEQ ID NO:9), artificial SSAL Th (SEQ ID NOS:10 and 11), a pathogen-derived Th (SEQ ID NO:12), and an immunostimulatory invasin peptide (Inv) taken from Yersinia (SEQ ID NO:13).

Completely synthetic peptide conjugates of the invention may be represented by the formulas:

$(A)_n$-(IgE-CH3 domain antigen)-$(B)_o$-$(Th)_m$-X.

or $(A)_n$-$(Th)_m$-$(B)_o$-(IgE-CH3 domain antigen)-X or $(A)_n$-$(B)_o$-$(Th)_m$-$(B)_o$-(IgE-CH3 domain antigen)-X or (IgE-CH3 domain antigen)-$(B)_o$-$(Th)_m$-$(A)_n$-X or $(Th)_m$-$(B)_o$-(IgE-CH3 domain antigen)-$(A)_n$-X wherein
    each A is independently an amino acid or a general immunostimulatory sequence;
    each B is chosen from the group consisting of amino acids,
        —NHCH(X)CH$_2$SCH$_2$CO—, —NHCH(X)CH$_2$SCH$_2$CO($\epsilon$-N)Lys-, —NHCH(X)CH$_2$S-succinimidyl($\epsilon$-N)Lys-, and —NHCH(X)CH$_2$S-(succinimidyl)-;
    each Th is independently a sequence of amino acids that constitutes a helper T cell epitope, or an immune enhancing analog or segment thereof;
    IgE-CH3 domain antigen is a peptide between about 25 and about 29 amino acids in length, is substantially homologous to one of the segments represented by SEQ ID NOS:5–8 and 84 of the CH3 domain of the epsilon heavy chain of a mammalian IgE antibody, and contains two cysteine residues separated by about 23 amino acid residues;
    X is an amino acid $\alpha$-COOH or $\alpha$-CONH$_2$;
    n is from 0 to about 10;
    m is from 1 to about 4; and
    o is from 0 to about 10.

More specifically, IgE-CH3 domain antigen is selected from the group consisting of SEQ ID NO:5, SEQ ID NO:6, SEQ ID NO:7, SEQ ID NO:8, homologous sequences from the epsilon heavy chain of mammalian IgE-CH3 antibodies, and crossreactive and immunologically functional analogs thereof.

The peptide compositions of the present invention comprises peptide immunogens from about 25 to about 100 amino acid residues, preferably from about 25 to about 80 amino acid residues and more preferably from about 45 to about 65 amino acid residues.

Also provided are adjuvants and/or delivery vehicles and other ingredients routinely incorporated with vaccine formulations, and instructions for dosage such that immunotherapeutic antibodies directed against the targeted IgE effector site are generated. This in turn inhibits the sensitization by circulatory IgE of basophils and mast cells, and thereby prevents the triggering and activation of mast cells/basophils by IgE-allergen complexes. The inhibitory mechanism, mediated by the antibodies and induced by the peptide composition of the present invention, will specifically reduce or eliminate the IgE-mediated pathology while leaving the defensive components of the immune system, e.g. IgG, unaffected.

DETAILED DESCRIPTION OF THE INVENTION

This invention is directed to novel peptide and peptide conjugate compositions for the generation of high titer polyclonal antibodies with specificity for a target effector site on the third domain of the Fc portion of IgE, i.e., the CH3 domain of the c chain.

For convenience, the term "peptide conjugate" as used herein refers to molecules which comprise Th epitopes covalently linked to IgE-CH3 domain antigen peptides, whether through conventional peptide bonds so as to form a single larger peptide, or through other forms of covalent linkage.

The high site-specificity of the compositions of this invention minimizes the generation of anti-IgE antibodies that can crosslink the bivalent IgE bound to Fc$\epsilon$R1 on the basophil/mast cell surface, and thereby evoke the production of non-anaphylactogenic anti-IgE antibodies. Therefore, the invention is further directed to a safe method for the treatment of IgE-mediated allergic diseases in mammals, including humans.

The targeted antigenic sequence was determined by a thorough screening of candidate sites on the CH2 and CH3 domains of human IgE for useful immunoreactivities. CH2 and CH3 sites were selected for synthesis as peptide immunogens based on the disclosures by Helm et al. (1988) and Presta et al. (1994) that a long region which begins in the carboxyl terminus region of the CH2 domain of IgE and proceeds through the CH3 domain contains potential effector sites. Potential loop structures in the conformation of IgE were deduced from a theoretical model for the three dimensional structure of human IgE made available by the Brookhaven National Laboratory at internet address http://www.pdb.bnl.gov/pdb.bin/pdbids and reported in Helm et al. (*Eur J Immunol*, 1991; 21: 1543–1548). Disulfide-bonded loops were incorporated into the design of selected peptide immunogens so as to mimic the positions of predicted loops, so as to maximize the possibility of crossreactivity between the designed target antigenic peptides and the native IgE molecule. Potential target antigenic sites were synthesized and made immunogenic either by chemical conjugation to KLH following solid-phase peptide synthesis, or by covalent attachment to promiscuous Th epitopes and other immunostimulatory sequences by continuous synthesis (Table 2). Several sites were synthesized as cyclic peptides, with the incorporation of specific disulfide bonds, so as to stabilize the mobile peptides into conformations that resemble predicted IgE loop structures. Potentially useful effector target sites were then identified by the preparation of hyperimmune sera and testing of the antiserum for crossreactivity to human IgE. Antibodies from sera with high crossreactivity to human IgE were purified and evaluated for ability to inhibit the IgE-mediated sensitization of human basophils in an in vitro assay for histamine release. Anti-peptide antibodies evoked by peptides, SEQ ID NOS: 14 and 15 comprising SEQ ID NO:5, displayed strong crossreactivity for IgE (Table 2), and most consistently displayed high inhibitory activity in the histamine release assay (Table 3). The target epitope common to the peptides of SEQ ID NOS:14 and 15 corresponds to a segment of the IgE CH3 domain shown in Table 1. Table 1 shows the amino acid sequence of CH2, CH3 and CH4 domains of the $\epsilon$ heavy chain of the human IgE aligned with the homologous'sequences taken from the dog, rat, and mouse. The target site on the human $\epsilon$ chain sequence that was determined to be useful for representation as the IgE-CH3 domain antigens of the invention is underlined in Table 1 and includes human $\epsilon$ chain residues 413–435. Homologous target sequences in the dog, rat, and mouse proteins are also underlined in Table 1. The homologous sequence in the horse is residues 296–318 in the amino acid sequence of Navarro et al., *Molec. Immunol.*, 1995, 32:1–8.

The underlined target IgE CH3 effector sites, and the derived IgE-CH3 domain antigen peptides of this invention, are short peptide sequences which, when synthesized by themselves, are usually weakly or non-immunogenic, more so for being self-antigens. These short peptides can be immunopotentiated by chemically coupling to a carrier protein, for example, keyhole limpet hemocyanin (KLH). A disadvantage of such "IgE-CH3 domain antigen-carrier protein" based immunogens is the weak immunogenicity of the antigen compared to the large carrier protein, an inherent problem associated with peptide-carrier protein conjugates. The majority of antibodies generated by such a conjugate are non-functional antibodies directed against the carrier protein. The preferred immunogens of the present invention are wholly synthetic peptides which minimize the generation of irrelevant antibodies, and thereby elicit immune responses more focused to the target IgE-CH3 domain antigens, e.g., SEQ ID NOS:5–8 and 84.

However, because the short IgE-CH3 domain antigen peptides of the present invention (e.g., SEQ ID NOS:5–8 and 84) are non-immunogenic T cell-dependent epitopes, they are dependent for immunogenicity on extrinsic Th epitopes. These are provided for the preferred peptides of the invention as covalently linked promiscuous Th epitopes. The immunogens of the invention elicit site-specific immunoreactivity to provide precise targeting of the effector site and thus produce non-crosslinking anti-IgE antibodies. The resultant site-specific antibodies inhibit sensitization and allergic response but do not induce spontaneous degranulation.

Specific examples are provided in the present invention as embodiments of the immunogenic peptide conjugates of the invention. These examples provide for the linkage of synthetic immunostimulatory elements to IgE-CH3 domain antigen peptides (e.g., SEQ ID NOS:5–8 and 84) such that potent crossreactive antibodies are broadly generated, in a genetically diverse host population, against the targeted site on the IgE CH3 domain. These anti-IgE antibodies are non-anaphylactogenic and specifically directed against IgE (Examples 2 and 3). These antibodies, in turn, lead to inhibition of histamine release and diminished IgE-mediated responses, thus resulting in effective treatment and/or prevention of IgE-mediated allergic diseases.

For active immunization, the term "immunogen" referred to herein relates to a peptide conjugate composition which is capable of inducing antibodies against an effector site present on the third domain of the ε-heavy chain of IgE (e.g., SEQ ID NOS:5–8 and 84), leading to inhibition or suppression of IgE-mediated basophil and mast cell degranulation. The peptide compositions of the present invention include IgE-CH3 domain antigen peptides, preferably linked to carrier proteins via chemical coupling, more preferably IgE-CH3 domain antigen peptides linked to promiscuous helper T cell epitopes (Th epitopes) via chemical coupling, and most preferably wholly synthetic peptides which contain IgE-CH3 domain antigen sequences and promiscuous helper T cell epitope (Th epitope) sequences.

The carrier proteins are covalently attached to the IgE-CH3 domain antigen peptides, preferably with a spacer (e.g., Lys-Lys-Lys), via chemical coupling. The Th peptides (e.g., SEQ ID NOS:9–12) are covalently attached to the IgE-CH3 domain antigen peptides (e.g., SEQ ID NOS:5–8 and 84) either via chemical-coupling or preferably via direct synthesis, preferably with a spacer (e.g., Gly-Gly), so as to be adjacent to either the N- or C-terminus of the IgE-CH3 domain antigen sequences, in order to evoke efficient antibody responses. The immunogen optionally may also comprise a general immunostimulatory amino acid sequence, for example one corresponding to a domain of an invasin protein from the bacteria Yersinia spp (Brett et al., *Eur J Immunol*, 1993, 23: 1608–1614) (SEQ ID NO:13). The general immunostimulatory sequence may comprise an optional spacer through which it is attached to a Th peptide.

The completely synthetic peptides of this invention can be represented by the formulas:

(A)$_n$-(IgE-CH3 domain antigen)-(B)$_o$-(Th)$_m$-X or (A)$_n$-(Th)$_m$-(B)$_o$-(IgE-CH3 domain antigen)-X or (A)$_n$-(B)$_o$-(Th)$_m$-(B)$_o$-(IgE-CH3 domain antigen)-X or (IgE-CH3 domain antigen)-(B)$_o$-(Th)$_m$-(A)$_n$-X or (Th)$_m$-(B)$_o$-(IgE-CH3 domain antigen)-(A)$_n$-X wherein
  each A is independently an amino acid or a general immunostimulatory sequence;
  each B is chosen from the group consisting of amino acids,
  —NHCH(X)CH$_2$SCH$_2$CO—, —NHCH(X)CH$_2$SCH$_2$CO (ε-N)Lys-, —NHCH(X)CH$_2$S-succinimidyl(ε-N)Lys-, and —NHCH(X)CH$_2$S-(succinimidyl)-;
  each Th is independently a sequence of amino acids that constitutes a helper T cell epitope, or an immune enhancing analog or segment thereof;
  IgE-CH3 domain antigen represents the sequence of an IgE-CH3 domain antigen peptide as defined herein (or a crossreactive and immunologically functional analog thereof);
  n is from 0 to about 10;
  m is from 1 to about 4; and
  o is from 0 to about 10.

The peptide immunogen of the present invention comprises from about 25 to about 100 amino acid residues, preferably from about 25 to about 80 amino acid residues and more preferably from about 25 to about 65 amino acid residues.

When A is an amino acid, it can be any non-naturally occurring or any naturally occurring amino acid. Non-naturally occurring amino acids include, but are not limited to, D-α-amino acids, β-alanine, ornithine, norleucine, norvaline, hydroxyproline, thyroxine, γ-amino butyric acid, homoserine, citrulline and the like. Naturally-occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. Moreover, when n is greater than one, and two or more of the A groups are amino acids, then each amino acid may be independently the same or different.

When A is an invasin domain, it is an immune stimulatory epitope from the invasin protein of a Yersinia species. This immune stimulatory property results from the capability of this invasin domain to interact with the β1 integrin molecules present on T cells, particularly activated immune or memory T cells. The specific sequence for an invasin domain found to interact with the β1 integrins has been described by Brett et al. (*Eur J Immunol*, 1993). A preferred embodiment of the invasin domain (Inv) for linkage to a promiscuous Th epitope has been previously described in U.S. Pat. No. 5,759,551 which is incorporated herein by reference. The Inv domain has the sequence Thr-Ala-Lys-Ser-Lys-Lys-Phe-Pro-Ser-Tyr-Thr-Ala-Thr-Tyr-Gln-Phe (SEQ ID NO:13) or is an immune stimulatory homologue thereof from the corresponding region in another Yersinia species invasin protein. Such homologues thus may contain substitutions, deletions or insertions of amino acid residues to accommodate bacterial strain variation, provided that the homologues retain immune stimulatory properties. An immune stimulatory homologue may also comprise an optional spacer through which it is attached to a Th epitope.

In one embodiment, n is 3 and (A)$_3$ is an invasin domain (Inv), glycine and glycine, in that order.

(B)$_o$ is an optional spacer and comprises amino acids which can be naturally occurring or the non-naturally occurring amino acids as described above. Each B is independently the same or different. The carrier proteins are covalently attached to the peptides with a spacer (e.g., Lys-Lys-Lys) via chemical coupling. The amino acids of B can also provide a spacer, e.g., Gly-Gly or (□-N)Lys, between the promiscuous Th epitope (e.g., SEQ ID NO:9) and the IgE-CH3 peptide (e.g., SEQ ID NO:5) and crossreactive and functional immunological analogs thereof. In addition to physically separating the Th epitope from the B cell epitope, i.e., the IgE-CH3 peptide (e.g., SEQ ID NO:5) and immunological analogs thereof, the spacer can disrupt any artifactual secondary structures created by the joining of the Th epitope with the IgE-CH3 peptide (e.g., SEQ ID NO:5) and crossreactive and functional immunological analogs thereof and thereby eliminate interference between the Th and/or B cell responses. The amino acids of B can also form a spacer which acts as a flexible hinge that enhances separation of the Th and IgE domains. Examples of sequences encoding flexible hinges are found in the immunoglobulin heavy chain hinge region. Flexible hinge sequences are often proline rich. One particularly useful flexible hinge is provided by the sequence Pro-Pro-Xaa-Pro-Xaa-Pro (SEQ ID NO:16), where Xaa is any amino acid, and preferably aspartic acid. The conformational separation provided by the amino acids of B permits more efficient interactions between the presented peptide immunogen and the appropriate Th cells and B cells and thus enhances the immune responses to the Th epitope and the antibody-eliciting epitope and their crossreactive and functional immunological analogs thereof.

Th is a sequence of amino acids (natural or non-natural amino acids) that comprises a Th epitope. A Th epitope can consist of a continuous or discontinuous epitope. Hence not every amino acid of Th is necessarily part of the epitope. Accordingly, Th epitopes, including analogs and segments of Th epitopes, are capable of enhancing or stimulating an immune response to the IgE-CH3 antigen peptides (e.g., SEQ ID NOS:5–8 and 84, and immunological analogs thereof). Th epitopes that are immunodominant and promiscuous are highly and broadly reactive in animal and human populations with widely divergent MHC types (Partidos et al., 1991; U.S. Pat. No. 5,759,551). The Th domain of the subject peptides has from about 10 to about 50 amino acids and preferably from about 10 to about 30 amino acids. When multiple Th epitopes are present (i.e. m≧2), then each Th epitope is independently the same or different. Th segments are contiguous portions of a Th epitope that are sufficient to enhance or stimulate an immune response to the IgE-CH3 peptide (e.g., SEQ ID NO:5) and immunological analogs thereof.

Th epitopes of the present invention include as examples, but are not limited to, pathogen-derived hepatitis B surface and core antigen helper T cell epitopes (HBs Th and HBc Th), pertussis toxin helper T cell epitopes (PT Th), tetanus toxin helper T cell epitopes (TT Th), measles virus F protein helper T cell epitopes (MVF Th), *Chlamydia trachomatis* major outer membrane protein helper T cell epitopes (CT Th), diphtheria toxin helper T cell epitopes (DT Th), *Plasmodium falciparum* circumsporozoite helper T cell epitopes (PF Th), *Schistosoma mansoni* triose phosphate isomerase helper T cell epitopes (SM Th), and *Escherichia coli* TraT helper T cell epitopes (TraT Th). The pathogen-derived Th were listed as SEQ ID NOS:2–9 and SEQ ID NOS:42–52 in U.S. Pat. No. 5,759,551; as Chlamydia helper site P11 in Stagg et al., *Immunology*, 1993; 79:1–9 (also listed here as SEQ ID NO:12); and as HBc peptide 50–69 in Ferrari et al., *J Clin Invest*, 1991; 88: 214–222, and are incorporated herein by reference.

Exemplary Th sites of the invention also include the artificial Th site termed "Syn Th (1,2,4)" (SEQ ID NO:9), artificial SSAL Th sites "(1,4,9 PALINDROMIC) Th", "IS (1,4,9 PALINDROMIC) LF Th" and "IS (1, 4, 9 PALINDROMIC)LF simplified Th" (SEQ ID NOS:10, 11 and 60), and immunologically functional analogs thereof. Functional Th analogs include immune-enhancing analogs, crossreactive analogs and segments of any of these Th epitopes. Functional Th analogs further include conservative substitutions, additions, deletions and insertions of from one to about 10 amino acid residues in the Th epitope which do not essentially modify the Th-stimulating function of the Th epitope.

The synthetic peptide of this invention are generally about 50 to about 90 amino acids, and comprise
  (a) an immunostimulatory invasin domain,
  (b) a helper T cell (Th) epitope, and
  (c) an IgE-CH3 domain antigen peptide.

More specifically, the synthetic peptides of this invention are described by the formulas (A)$_n$-(Th)$_m$-(B)$_o$-(IgE-CH3 domain antigen)-X, (A)$_n$-(B)$_o$-(Th)$_m$-(B)$_o$-(IgE-CH3 domain antigen)-X, (A)$_n$(IgE-CH3 domain antigen)-(B)$_o$-(Th)$_m$-X, (IgE-CH3 domain antigen)-(B)$_o$-(Th)$_m$-(A)$_n$-X, and (Th)$_m$-(B)$_o$-(IgE-CH3 domain antigen)-(A)$_n$-X.

The Th epitope is attached, optionally through spacer B, to either the N terminus or C terminus of the IgE-CH3 peptide and crossreactive and functional immunological analogs thereof. Preferred peptide immunogens of this invention are the peptides containing the IgE-CH3 domain antigen peptides (e.g., SEQ ID NO:5) (or immunological analogs thereof) and Th peptides, and optionally Inv (SEQ ID NO:13). In a more preferred embodiment the Th epitope is an HBs Th, HBc Th, MV$_F$ Th, PT Th, TT Th, CT Th (e.g., SEQ ID NO:12) or artificial Th (SEQ ID NOS:9–11 and 60), or functional immunogenic analogue thereof, and optionally, A is Inv (SEQ ID NO:13) attached through a (B)$_o$ spacer such as Gly-Gly or (□-N)Lys.

The structure of the IgE-CH3 domain antigen comprises a peptide sequence taken from the CH3 domain of human IgE (amino acids 413–435 of SEQ ID No:1) or the homologous sequences from other species (e.g., SEQ ID NOS:6–8 and 84) and subjected to the following modifications:
  the target site is modified from that of the naturally occurring IgE sequences by the insertion of a cysteine residue to the N-terminus side of position 413 or homologous position unless cysteine is already present at positions 413 or 414 in the natural sequence,
  the substitution for the native cysteine of position 418 or corresponding position of an homologous non-human sequence or any other cysteine of the native target sequence by serine (unless said native cysteines are present at positions 413 or 414 and 435 or 436),
  the insertion of cysteine at C-terminus side of position 435 or homologous position unless cysteine is already present at positions 435 or 436 in the natural sequence, and
  the formation of a disulfide bond between the retained cysteines so as to produce a cyclic structure.

Said cyclic structures also comprise 1 to 5 additional amino acids taken from either terminus of the 413–435 segment of IgE provided that the single disulfide looped structure is preserved. An optimized target antigen for human IgE of sequence Cys-Gly-Glu-Thr-Tyr-Gln-Ser-Arg-Val-Thr-His-Pro-His-Leu-Pro-Arg-Ala-Leu-Met-Arg-Ser-Thr-Thr-Lys-Cys (SEQ ID NO:5) is provided by the present invention. The human IgE target antigen is cyclized through the unnatural terminal cysteines and the first serine residue substitutes for the cysteine residue of the natural sequence. Antibody that is evoked by peptide immunogens comprising this IgE-CH3 domain antigen is crossreactive with human IgE and inhibits the sensitization of human basophils by human IgE.

Likewise, corresponding IgE-CH3 domain antigen sequences for IgE of other species can be derived from the homologous ε chain segment of the relevant species. For example, such target sequences can be taken from the dog, rat and mouse ε chain sequences shown in Table 1 as SEQ ID NOS:2, 3 and 4, and the equine sequence published by Navarro et al., and IgE-CH3 domain antigen sequences such as SEQ ID NOS:6, 7, 8 and 84 can be derived.

Crossreactive and immunologically functional analogs of the IgE-CH3 domain antigen peptides (e.g., SEQ ID NOS:5–8 and 84) according to the invention, may further comprise conservative substitutions, additions, deletions, or insertions of from one to about four amino acid residues, provided that the resulting peptide analogs are capable of eliciting immune responses crossreactive with the IgE-CH3 peptides (e.g., SEQ ID NOS:5–8 and 84). The conservative substitutions, additions, and insertions can be accomplished with natural or non-natural amino acids as defined herein.

Peptide compositions which contain mixtures of the subject peptide immunogens with two or more of the Th epitopes may enhance immunoefficacy in a broader population and thus provide an improved immune response to the IgE-CH3 domain antigen (e.g., SEQ ID NOS:5–8 and 84).

The peptide immunogens of this invention can be made by chemical synthesis methods which are well known to the ordinarily skilled artisan. See, for example, Fields et al., Chapter 3 in *Synthetic Peptides: A User's Guide*, ed. Grant, W. H. Freeman & Co., New York, N.Y., 1992, p. 77. When a peptide immunogen includes a SSAL Th, the coupling of the alternative amino acids at a given variable position is accomplished by providing a mixture of the amino acids specified for that position. Hence, peptides can be synthesized using the automated Merrifield techniques of solid phase synthesis with the α-NH$_2$ protected by either t-Boc or Fmoc chemistry using side chain protected amino acids on, for example, an Applied Biosystems Peptide Synthesizer Model 430A or 431.

After complete assembly of the desired peptide immunogen, the resin is treated according to standard procedures to cleave the peptide from the resin and deblock the functional groups on the amino acid side chains. The free peptide is purified, for example by HPLC, and characterized biochemically, for example, by amino acid analysis, mass spectrometry, and/or by sequencing. Purification and characterization methods for peptides are well known to those of ordinary skill in the art.

Other chemical means to generate the synthetic peptide constructs of the invention containing IgE and Th sites include the ligation of haloacetylated and cysteinylated peptides through the formation of a "thioether" linkage. For example, a cysteine can be added to the C terminus of a Th-containing peptide and the thiol group of cysteine may be used to form a covalent bond to an electrophilic group such as an N chloroacetyl-modified or a maleimide-derivatized α- or ε-NH$_2$ group of a lysine residue attached to the N-terminus of an IgE-CH3 peptide (e.g., SEQ ID NO:5) or crossreactive and functional immunological analogs thereof. In this manner, a construct with Th-(IgE-CH3 domain antigen) or its reverse, (IgE-CH3 domain antigen)-Th, may be obtained.

The subject immunogen may also be polymerized. Polymerization can be accomplished for example by reaction of the immunogen with a cross-linking agent, for example by reaction between glutaraldehyde and the —NH$_2$ groups of lysine residues, using routine methodology. By another method, a synthetic immunogen, such as for example "A-Th$_m$-spacer-(IgE-CH3 domain antigen)", can be polymerized or co-polymerized with another immunogen by utilization of an additional cysteine added to the N-terminus of the synthetic immunogen. The thiol group of the N-terminal cysteine can be used for the formation of a "thioether" bond with haloacetyl-modified amino acid or a maleimide-derivatized α-NH$_2$ or ε-NH$_2$ group of a lysine residue that is attached to the N-terminus of a branched poly-lysyl core molecule (e.g., K$_2$K, K$_4$K$_2$K or K$_8$K4K$_2$K). The subject immunogen may also be prepared as a branched polymer through synthesis of the desired peptide construct directly onto a branched poly-lysyl core resin (Wang et al., *Science*, 1991; 254: 285–288).

Alternatively, the longer synthetic peptide immunogens can be synthesized by well-known recombinant DNA techniques. Many standard manuals on molecular cloning technology provide detailed protocols to produce the peptides of the invention by expression of recombinant DNA and RNA. To construct a gene encoding a peptide of this invention (e.g., immunogenic peptides comprising SEQ ID NOS:5–8 and 84, and other species-specific homologs), the amino acid sequence is reverse translated into a nucleic acid sequence, preferably using optimized codon usage for the organism in which the gene will be expressed. Next, a gene encoding the peptide is made, typically by synthesizing overlapping oligonucleotides which encode the peptide and necessary regulatory elements. The synthetic gene is assembled and inserted into the desired expression vector. The synthetic nucleic acid sequences encompassed by this invention include those which encode the peptides of the invention, immunologicaly functional homologs, and nucleic acid constructs characterized by changes in the non-coding sequences that do not alter the immunogenic properties of the peptide encoded thereby. Nucleic acids which comprise sequences that encode the peptides of this invention are also provided. The synthetic gene is inserted into a suitable cloning vecor and recombinants are obtained and characterized. The peptide is then expressed under conditions appropriate for the selected expression system and host. The peptide is purified and characterized by standard methods.

The nucleic acids of this invention may themselves be useful as components of so-called "DNA vaccines". In this embodiment of the invention, expression of the immunogenic peptides of the invention is induced in the patient's own cells, by introduction into those cells of nucleic acids which encode the peptides. Methods of making and using DNA vaccines are disclosed in U.S. Pat. Nos. 5,580,859, 5,589,466, and 5,703,055; see also WO 97/02840 and W. McDonnell and F. Askari, *New Engl. J. Med.*, 1996, 334:2–45, all of which are incorporated herein by reference. Such methods of making and using the peptides and peptide conjugates of this invention are contemplated to be within the scope of this invention.

The efficacy of any peptide composition of the present invention can be established by in vitro assay in which a host animal is immunized with a peptide composition of the invention and the resulting antibodies are shown to inhibit the sensitization of basophils and mastcells by IgE, as shown in Examples 2 and 6. Efficacy can be established in vivo by injecting a host with a species-appropriate peptide composition (for example, immunizing mice with a formulation of immunogens comprising SEQ ID NOS:24 and/or 25) followed by monitoring the humoral immune response to the IgE-CH3 peptide and crossreactive and functional immunological homologues thereof, as detailed in Example 5.

Another aspect of this invention provides a peptide composition comprising an immunologically effective amount of one or more of the peptide immunogens of this invention in a pharmaceutically acceptable delivery system. Accordingly, the subject peptides can be formulated as a pharmaceutical composition using adjuvants, pharmaceutically acceptable carriers, or other ingredients routinely provided in vaccine compositions. Among the ingredients that can be used in this invention are adjuvants or emulsifiers including alum, incomplete Freund's adjuvant, liposyn, saponin, squalene, L121, emulsigen, monophosphoryl lipid A (MPL), QS21, ISA51, ISA35, ISA 206, and ISA 720, as well as other known efficacious adjuvants and emulsifiers. The formulations include formulations for immediate release and/or for sustained release, and for induction of systemic immunity and/or induction of localized mucosal immunity, which may be accomplished by, for example, immunogen entrapment by or coadministration with microparticles. Such formulations are readily determined by one of ordinary skill in the art, and methods for the preparation, preservation, and sterilization of such formulations are known to those skilled in the art.

The present pharmaceuticals can be administered by any convenient route including subcutaneous, oral, intramuscular, or other parenteral or enteral route. Similarly the pharmaceuticals can be administered as a single dose or multiple doses. Immunization schedules are readily determined by the ordinarily skilled artisan.

The pharmaceutical composition of the instant invention contain an effective amount of one or more of the peptide immunogens of the present invention and a pharmaceutically acceptable carrier. Such a composition in a suitable dosage unit form generally contains about 0.5 $\mu$g to about 1 mg of the immunogen per kg body weight. When delivered in multiple doses, it may be conveniently divided into an appropriate amount per dosage unit form. For example, an initial dose, e.g. 0.2–2.5 mg; preferably 1 mg, of immunogen represented as a peptide composition of the present invention, may be administered by injection, preferably intramuscularly, followed by repeat (booster) doses. Dosage will depend on the age, weight and general health of the patient as is well known in the vaccine and therapeutic arts.

The immune response to synthetic IgE-CH3 peptide immunogens may be improved by delivery through entrapment in or on biodegradable microparticles of the type described by O'Hagan et al. (Vaccine, 1991; 9:768–771). The immnunogens can be encapsulated with or without an adjuvant in biodegradable, microparticles, to potentiate immune responses, including localized mucosal immunity which may be especially applicable to mucosally localized allergic reactions, and to provide time-controlled release for sustained or periodic responses, for oral administration, and for topical administration (O'Hagan et al., 1991; Eldridge et al., *Molec. Immunol.*, 1991; 28: 287–294).

The pharmaceutical compositions of this invention are used in a manner similar to that of vaccines, for the prevention of atopic allergic reactions including allergic rhinitis, those of food allergies, asthma, anaphylaxis, flea allergy dermatitis, and other IgE-mediated hypersensitivities.

All patents and literature references referenced hereinabove are incorporated herein by reference.

Specific peptide and peptide conjugate immunogens are provided in the following examples to illustrate the invention. These examples are for purpose of illustration only, and are not to be construed as limiting the scope of the invention in any manner.

EXAMPLE 1

Identification of Potential Effector Sites on the Human IgE Molecule

Peptide Design

Sites within the CH2 and CH3 domains of $\epsilon$ heavy chain of human IgE were selected for mimicry by peptides, in accordance with the disclosures of Helm et al. (1988) and Presta et al. (1994) that a long segment of the $\epsilon$ chain which overlaps both these domains participates in binding IgE to the Fc$\epsilon$R1 receptor. The sequences of such sites were synthesized as target site peptides and rendered into antigens by (1) attaching them through chemical coupling to large carrier proteins such as KLH or (2) constructing peptides where promiscuous Th and Inv (SEQ ID NO:13) were linked to the amino terminal of the target sites. Specific sites within these domains were selected as peptides for cyclization based on predictions by the Brookhaven 3-dimensional model for human IgE (http:www.pdb.bnl.gov/pdb.bin/pdbids) of surface-exposed loops. Specified cyclic constraints were installed into the design of those peptides so as to maximize the crossreactions between the antigens and the native IgE molecule. Accordingly, several of the synthetic constructs were synthesized with introduced cysteines not found in the native sequence to produce disulfide bond loops of specified position, in mimicry of loop structures predicted by the Brookhaven model. In some cases naturally occurring cysteines were substituted with serines so as to prevent the formation of conformations not favored by the model.

The constructs are listed in Table 2. Peptides marked by * in the description column of Table 2 are cyclized by cysteine disulfide bonds. Cysteine residues that have been inserted into the native sequence for cyclization are denoted in the amino acid sequences of Table 2 by parentheses, other residues that have been inserted, substituted for a native residue, or are natural cysteines that participate in disulfide bonds are indicated in the amino acid sequences of Table 2 by underlining. Other peptides are linear. Peptides labeled by "a" in the third column represent the IgE-CH2/3 or —CH3 antigen peptide, chemically linked to KLH carrier protein by conventional glutaraldehyde or MBS (m-Maleimidobenzoyl-N-hydroxysuccinimide ester, Pierce Chemical Co., catalogue No. 22510) coupling reactions. Peptides marked by "b" in the third column were synthesized as IgE antigen peptides in tandem with the Th sites shown. Th sites used include the HBs$_{19-32}$ Th taken from hepatitis B virus, the MVf Th taken from measles virus, and PT$_{149-146}$ Th taken from pertussis toxin as referenced in U.S. Pat. No. 5,759,551, the CT Th termed P11 (Stagg et al., 1993) and novel artificial Th sites termed "1,4,9 PALINDROMIC Th" (SEQ ID NO:10), "IS(1,4,9 PALINDROMIC)LF Th" (SEQ ID NO:11), "IS(1,4,9 PALINDROMIC)LF simplified Th" (SEQ ID NO:60), and "Syn Th (1,2,4)" (SEQ ID NO:9). Peptides marked by "c" are variants of the "b" constructs synthesized in tandem with the Inv domain immunostimulatory peptide (SEQ ID NO:13).

The "b" and "c" constructs were also synthesized with Gly-Gly spacers for separation of the IgE-CH2/3 or —CH3 target antigen site from the Th site, and separation of the Th from the Inv immunostimulatory site. The "b" and "c" constructs in Table 2 had the Th and/or Inv domains attached to the amino terminal of the IgE target site. The peptide immunogens of Table 2 were screened as candidate target antigenic peptides for the treatment of allergy, by the hyperimmunization of animals followed by testing of the hyperimmune sera for crossreactivity to human IgE.

Specific Procedures for the Screening of Candidate Target Antigenic Peptides

1. Synthesis of IgE-CH3 Domain Antigen Peptides and Conjugates.

Peptides listed in Table 2 were synthesized by the Merrifield solid-phase synthesis technique on Applied Biosystems automated peptide synthesizers using Fmoc chemistry. When a peptide immunogen included a SSAL Th, the coupling of one of the alternate amino acids at a given variable position was accomplished by providing a mixture of amino acids at equivalent molar ratios. After complete assembly of the desired peptide, the resin was treated according to standard procedure using trifluoroacetic acid to cleave the peptide from the resin and deblock the protecting groups on the amino acid side chains. For cyclic peptides, the cleaved peptides were dissolved in 15% DMSO in water for 48 hours to facilitate intradisulfide bond formation between cysteines.

2. Experimental Immunizations.

Rats or guinea pigs were immunized intramuscularly with experimental peptide immunogens. The dose was 100 $\mu$g of peptide suspended in a volume of 0.5 ml. The first dose was administered with Complete Freunds Adjuvant. Subsequent doses were administered in Incomplete Freunds Adjuvant. Animals received injections on weeks 0, 3, 6, and 10 or 0, 2, 4, and 8. Test bleeds were taken at, biweekly intervals and reactivities were determined by IgE peptide ELISA and crossreactivities by human IgE ELISA.

3. ELISA Assays.

Peptide ELISAs for-determination of anti-IgE peptide reactivity were conducted in peptide-coated 96-well microtiter plates coated by 1 hr incubation at 37° C. with an appropriate "a" target antigen site peptide without carrier at 0.5 $\mu$g/mL using 100 $\mu$L per well in 10 mM $NaHCO_3$ buffer, pH 9.5. For determination of anti-human IgE crossreactivity, human IgE ELISAs were conducted in human IgE-coated 96-well microtiter plates coated in a likewise fashion with a human IgE myeloma protein (American Biosystems, Inc. cat. no. A113) at 5 $\mu$g/mL. The peptide or human IgE-coated wells were incubated with 250 $\mu$L of 3% by weight of gelatin in PBS, at 37° C. for 1 hr to block non-specific protein binding sites, washed three times with PBS containing 0.05% by volume TWEEN 20 and then dried. Test samples were serially diluted with PBS containing 20% by volume normal goat serum, 1% by weight gelatin and 0.05% by volume TWEEN 20. 100 $\mu$L of the diluted sample was added to each of the wells and allowed to react for 1 hr at 37° C. The wells were then washed six times with 0.05% by volume TWEEN 20 in PBS to remove unbound labeled antibodies. 100 $\mu$L of horseradish peroxidase labeled anti-rat IgG goat antibody or anti-guinea pig IgG goat antibody at predetermined optimal dilution in 1% by volume normal goat serum, 0.05% by volume TWEEN 20 in PBS were added to each well and incubated at 37° C. for 30 minutes. The wells were washed six times with 0.05% by volume TWEEN 20 in PBS to remove unbound labeled antibody conjugate and reacted with 100 $\mu$L of the substrate mixture containing 0.04% by weight orthophenylenediamine (OPD) and 0.12% by volume hydrogen peroxide in sodium citrate buffer pH 5.0, for 15 minutes. Reactions were stopped by the addition of 100 $\mu$L of 1.0 M $H_2SO_4$ and the absorbance at $A_{492}$ was measured. ELISA titers, expressed as $\log_{10}$ of reciprocal dilution, were calculated based on linear regression analysis of the absorbances, with cutoff $A_{492}$ set at 0.5. This cutoff value was rigorous as the values for diluted normal guinea pig control samples run with each assay were less than 0.15.

Results

Candidate target antigen sites are described in Table 2. They are shown either as "a" peptides attached to KLH carrier or as "b" peptides attached to synthetic Th sites or as "c" peptides attached to synthetic Th and Inv. Either rats or guinea pigs were immunized as described in Specific Procedures above and hyperimmune antisera collected at week 8 were analyzed by anti-peptide ELISA and anti-human IgE ELISA as described in Specific Procedures.

Many of the CH2/3 and CH3 peptide immunogens were immunogenic, as they evoked anti-peptide antibodies with titers in the range of $\log_{10}$ 2–5. The CH2/3 antigenic target sites comprising long segments of the human $\epsilon$ chain from 301–376 (numbering scheme of Table 1) were all strongly crossreactive with human IgE, as shown by $\log_{10}$ titers on the anti-human IgE ELISA of greater than 3. Crossreactivity was lost for some CH3 peptides which initiated at position 342 and beyond (e.g., entries 21 and 22). However, for CH3 peptides which included a relatively short region comprising 354–372, crossreactivity was largely restored (e.g., entries 27, 28, and 29) with the exception of entry 31 (354–368). Another short region of crossreactivity is seen in entry 20 (cyclic peptide spanning positions 374–385).

As evidenced by the lack of crossreactivity of entries 14, 17, 23, 24, 25, and 26, a stretch of sequence that extends from 365 to 413 is devoid of crossreactivity, despite overlap with the 354–372 region of crossreactivity and a crossreactive region represented by entry 20 (374–385). Interestingly, the short crossreactivities exemplified by entries 27, 28, 29 (354–372) and 20 (374–385) are lost in the conformation of the long cyclized peptide entry 17 (365–396), despite their overlap in those crossreactive regions. Crossreactive sites which overlap non-crossreactive sites are again to be found beyond a region that starts around position 399 and extends to position 445, as shown by the crossreactivities of entries 15 and 30, and the weak crossreactivities of entries 19 (432–445) and 23 (404–413). It is significant that of two similarly cyclized peptides which include position 418, 15 (413–435) and 18 (404–434), only entry 15 (SEQ ID NO:5), in which the cysteine at position 418 has been substituted by serine, is crossreactive with human IgE. A CH4 site that corresponds to an IgE effector site described by Stanworth (Stanworth et al., *Lancet*, 1990; 336:1279–1281) failed to show crossreactivity (entry 34).

These results demonstrate that crossreactivity for IgE peptides is a complex phenomenon influenced by conformational features, and cannot be predicted from a straightforward analysis of overlapping linear peptides. Candidate IgE-CH3 domain antigens were selected from among the conjugates shown to be crossreactive with human IgE in Table 2 and used for further analyses.

EXAMPLE 2

Identification of Effector Site on the Human IgE Molecule

IgE-CH3 domain antigen peptides were selected for further analysis from among those peptide conjugates of Table 2 that exhibited high affinity crossreactivities to human IgE, as evidenced by anti-IgE titers for their respective antisera of greater than $\log_{10}=3$. Guinea pig hyperimmune sera were produced as described above. Guinea pig IgG antibodies were purified from the hyperimmune sera by protein A affinity chromatography and analyzed by a functional assay for determination of ability of anti-IgE to inhibit the sensitization of human basophils by allergen-specific IgE. The endpoint of the assay is expressed as per cent inhibition of IgE-mediated histamine release.

Guinea pig IgG antibodies were purified from serum by Protein A affinity chromatography (ImmunoPure® Immobilized Recomb® Protein A, Pierce) and the eluted antibodies were prepared at a standard concentration of 8 mg/ml in 25 mM PIPES buffer, 0.15 M NaCl, pH 7.2. A control antibody preparation was prepared from the pooled serum of guinea pigs immunized with an irrelevant peptide immunogen. These antibodies were used in assays that measure the reduction in IgE-mediated sensitization of human basophils. Human basophils were prepared from the venous blood of volunteers using centrifugation through Percoll density gradients (MacGlashan. *J Allergy Clin Immunol*, 1993; 91:605–615). The banded leukocytes were collected, washed, and resuspended in 0.1 ml of PAGCM buffer as described (MacGlashan, 1993) except that the PAGCM buffer used to suspend the cells was made up with water containing 44% $D_2O$. The IgE used for the assay was allergen-specific, either human BPO-specific IgE or chimeric human IgE specific for HIV glycoprotein gp120. The allergen-specific IgE used for sensitization at 0.25 µg/ml was preincubated with an equal volume of purified guinea pig antibody at 8 mg/ml, total volume 0.1 ml, for 15 minutes at 37° C., prior to being added to the basophils. The antibody mixture was added to the cells and incubated for 20 minutes to allow for sensitization of the cells by uncomplexed IgE. The sensitized cells were then stimulated by addition of the allergen, either $BPO_{21}$-HSA or a gp120 polypeptide as described (MacGlashan, 1993).

After an appropriate incubation period (usually 45 minutes), the cells were separated from the supernatant and the supernatant assayed for histamine content by an automated fluorimetric technique (Siraganian, *Anal Biochem*, 1974; 57: 383–394). All reactions were performed in duplicate. The percentage of histamine release was calculated from the ratio of sample to total histamine after spontaneous release was subtracted from both. Results are expressed as per cent inhibition of histamine release, as determined from the ratio of histamine release by experimental antibody to histamine release by the control antibody of irrelevant specificity. Histamine release assays on human basophils were kindly performed under coded conditions by Dr. Donald W. MacGlashan, The Johns Hopkins University School of Medicine, Johns Hopkins Asthma and Allergy Center, Baltimore.

Results

The results for inhibition of histamine release assays are shown in Table 3 for guinea pig anti-peptide antibodies that displayed crossreactivities for human IgE of $\log_{10}>3$. Determinations were made from antibodies purified from 8 week bleeds, except for antibodies against peptide entries 15b and 15c which were also characterized from serum collected on week 12. The inhibition results shown for anti-15b and anti-15c antibodies, of 61% and 71%, were made on the antibodies purified from bleeds taken on weeks 8 and 12, respectively. Separate animals had been immunized with 15b and 15c, but antibodies from both sets of animals had been pooled for the 8 and 12 week results shown in Table 3. (The guinea pigs of these groups had received an additional dose of peptide conjugate on week 10 and so had retained high antibody levels for the 12 week bleed). The significant inhibitory reactivity of the anti-15 antibodies was unexpected in comparison to the reactivities of the IgE crossreactive antibodies evoked by the remainder of the peptides shown in Table 3. These other IgE-CH3 domain antigenic peptides failed to provide inhibition, or presented levels of inhibition for histamine release that were negligible and non-reproducible.

Histamine release inhibition results and IgE crossreactivities for antibodies elicited by IgE-CH3 domain antigen peptides that overlap with the antigenic site (SEQ ID NO:5) of peptide entries 15b (SEQ ID NO:14) and 15c (SEQ ID NO:15) may be compared. The IgE antigens represented by peptide entries 19, 23, 24, and 33 comprise short overlaps with the entry 15 antigen sequence (SEQ ID NO:5). They compare unfavorably to entry 15 for crossreactivity to IgE, and are devoid of inhibitory activity. The IgE antigen sequence (SEQ ID NO:44) of entry 18 comprises the entire antigen sequence of entry 15, except that (1) the carboxyl terminal lysine is deleted, (2) the naturally occurring cysteine at position 418 is retained, and (3) there are nine additional N-terminal amino acids. It is non-crossreactive with IgE and fails to inhibit histamine release. In contrast, the immunogens of entry 15, having antigen SEQ ID NO:5, provide unexpected reactivities. The IgE-CH3 domain antigen sequence of entry 15, with a cyclic structure specified by introduced terminal cysteines, and with no contribution from the cysteine at position 418 (which has been replaced), provides an antigen that is crossreactive with IgE and elicits antibodies which inhibit IgE sensitization.

Antibodies elicited by entry 15b (SEQ ID NO:14) and 15c (SEQ ID NO:15) were prepared from 13 week bleeds and tested individually. By week 13, both crossreactivity for IgE, as determined by IgE ELISA, and per cent inhibition of histamine release had diminished from the values of week 12. Nevertheless, antibodies from both preparations were found to be individually effective in reducing histamine release: anti-15b inhibited 28% and anti-15c inhibited 20%.

The extent by which histamine release was inhibited by either of these antibodies was dose dependent, as evidenced by the effect of dilution on the antibodies. When a preparation of anti-15b from week 13 was assayed at full concentration (8 mg/ml), then at 1:3 and 1:9 dilutions, per cent inhibition of histamine release was 28%, 21%, and 14% respectively.

A preparation of guinea pig anti-15b was tested by direct challenge of IgE-sensitized basophils, in the absence of allergen, as an evaluation of its ability to crosslink receptor-bound IgE and induce degranulation. Histamine release by anti-15b was equivalent to the level of spontaneous histamine release by the donor cells. This indicates that antibody of specificity for the SEQ ID NO:5 IgE antigen is non-anaphylactogenic. Thus, active immunization with peptide conjugate immunogens comprising the IgE-CH3 domain antigen SEQ ID NO:5 (SEQ ID NOS:14 and 15) elicits non-anaphylactogenic anti-IgE antibodies that inhibit IgE-mediated sensitization without themselves causing histamine release. These actively evoked polyclonal antibodies display specificity for an IgE effector site that has not been described by previous studies, including prior studies of therapeutic and non-anaphylactogenic anti-IgE monoclonal antibodies intended for treatment of allergy by passive immunization (U.S. Pat. No. 4,940,782, U.S. Pat. No. 5,420,251 and Presta et al., 1993).

EXAMPLE 3

Isotype Specificity and Potential for Immunosuppression

The polyclonal antibodies elicited by active immune response to SEQ ID NOS:14 and 15 were examined for specificity to IgE in comparison to IgG. Anti-15b guinea pig antibodies described in Example 2 that were prepared from the 12 week bleed were subjected to a parallel comparison of crossreactivities to IgE and IgG, by the IgE ELISA described in Example 1 and by a similar IgG ELISA. For the IgE ELISA, plates were coated with the human IgE myeloma at 5 μg/ml. For the IgG ELISA, the plates were coated with human purified IgG (Sigma reagent grade human IgG), also at 5 μg/ml. The purified guinea pig anti-15b was tested for reactivities in both ELISAs at concentrations of 0.5 and 0.1 μg/ml. Results were compared to antibodies purified from control guinea pig serum and to a "no antibody" control. The $A_{490}$ values for anti-15b antibody on IgE were 1.126 at 0.5 μg/ml and 0.344 at 0.1 μg/ml. The $A_{490}$ values for anti-15b antibody on IgG were equal to control antibody and background values. There was no crossreactivity of the guinea pig anti-15b to human IgG. The peptide composition of the invention did not evoke antibodies that recognize IgG antibodies, and therefore are isotype specific for IgE. They will suppress IgE-mediated allergic reactions and not result in undesirable immunosuppression of IgG protective antibody responses.

EXAMPLE 4

Representative Peptide Conjugates of the Invention

The immunogenic peptide conjugates of the invention shown in Table 4A, which are wholly synthetic peptides, were synthesized by the solid-phase method outlined in Example 1. Each peptide in the Table can be represented by the formula $(A)_n$-$(Th)_m$-$(B)_o$-(IgE-CH3 domain antigen)-X, but peptides of the other formulas disclosed above are understood to be encompassed within the peptides of this invention. The IgE-CH3 domain antigen sequence is SEQ ID NO:5, 6, or 8 in the peptides of Table 4A, but it is understood that homologous IgE-CH3 domain antigen sequences from other mammalian species are encompassed within the peptides of this invention. The immunogenic peptides comprise Th sites derived from foreign pathogens (e.g., SEQ ID NO:20, 87), and also artificial Th (e.g., SEQ ID NOS:14, 18, 21 and 90). In addition to the examples shown in Table 4A, other pathogen-related Th may be selected from among the promiscuous Th sites exemplified in Table 5, and artificial Th may be selected from among the Th sites exemplified in Table 6. Each peptide of this example has Gly-Gly or (□-N)Lys spacers between immunogenic elements, but peptides of the invention may have other spacers (e.g., SEQ ID NO:16) or no spacers.

Peptides of these examples also comprise an optional Inv immunostimulatory site (e.g., SEQ ID NOS:15–19 and 22). It is understood however that the invention is not limited to Inv as an additional immunostimulatory element. As shown by the KLH conjugate, peptide conjugates of the invention also include an IgE-CH3 domain antigen coupled to a carrier protein.

Materials and Methods

Representative peptide constructs of the invention as listed in Table 4A (SEQ ID NOS: 18, 85, 87, 88, 90 and 91) were synthesized, cleaved, cyclized and purified as described in Example 1. The peptide constructs were formulated for immunization into small animals such as guinea pigs, or into larger animals such as pigs or baboons for evaluation of their immunogenicities. Peptides were suspended in a volume of 0.5 mL containing. representative emulsifiers or adjuvants such as ISA51, ISA720, DDA or monophosphoryl lipid A (MPL). The dose was 100 μg of peptide for guinea pigs or 300 μg of peptide for swine or baboons and the animals were immunized intramuscularly.

Animals received injection on weeks 0, 3 and 6 or 0, 2 and 4 weeks as specified in Table 4B. Test bleeds from 8 weeks post initial immunization were evaluated for crossreactivities to IgE by human IgE or dog IgE ELISA as described in Example 1, except that for the dog IgE ELISA a dog IgE myeloma protein (Bethyl Laboratories Inc., Montgomery Tex.) was used for plate coating at 1 μg/mL, and horseradish peroxidase labeled protein A/G reagent (Pierce Chemical Co., Rockford Ill.) at a predetermined optimal dilution was used as the tracer for detection of dog IgE. The peptide-induced crossreactivities were also evaluated for capacity to inhibit IgE-mediated histamine release. Guinea pig, pig, or baboon IgG were purified from representative immune sera by protein A affinity chromatography and analyzed by functional assay for determination of ability to inhibit the sensitization of human basophils by allergen-specific IgE, as described in details in Example 2. The endpoint of the assay is expressed as per cent inhibition of IgE-mediated histamine release in comparison to control antibody of the same species that was raised with specificity for an irrelevant antigen, as shown in Table 4B.

Results

The representative peptide constructs were of relevant immunogenicity, as all peptides tested elicited strong site-directed cross reactivities to the corresponding human IgE or dog IgE, as shown by $Log_{10}$ titers on the anti-human IgE or anti-dog IgE ELISAs of greater than 3 (Table 4B). Inhibition of IgE-mediated sensitization was observed for guinea pig, pig, and baboon antibodies as evaluated by the ability of the anti-IgE peptide antibodies to inhibit histamine release by basophils. This functional crossreactivity by the baboon antibodies is noteworthy insomuch as the neutralization of human IgE by the baboon IgG is nearly a human system. Thus, the efficacy of a peptide construct of the invention, as an agent for the immunotherapy of allergy by active immunization, is indicated in a model that is nearly homologous for species of peptide and target species.

EXAMPLE 5

Immunization of Mice and Evaluation of In Vivo Efficacy

Efficacy of peptides of SEQ ID NOS:24 and 25 (37b and 38b) is evaluated with five groups of 16 mice by the immunization and sensitization protocol outlined below.

Groups of 16 mice (Balb/c), female, 8–10 weeks old, are immunized subcutaneously with the indicated peptide composition of the invention. The mice are given 20 μg/0.2ml doses on weeks 0, 3, 6, and 11. The first dose is prepared with Complete Freunds Adjuvant, subsequent doses with Incomplete Freunds Adjuvant. The mice are sensitized to a hapten conjugate, diphenylated KLH (DNP-KLH), on weeks 7 and 10. Sensitization is accomplished by intraperitoneal administration of DNP-KLH in 0.4% Alum, 5 μg/0.2ml/dose. Mock immunizations and sensitizations are accomplished in control groups by administration of adjuvant with phosphate-buffered-saline. The groups are as follows:

1: Immunize/mock sensitize, with peptide 37b and 0.4% Alum
2: Immunize/sensitize, with peptide 37b and DNP-KLH
3: Mock immunize/sensitize, with Freunds and DNP-KLH
4: Immunize/mock sensitize, with peptide 38b and 0.4% Alum
5: Immunize/sensitize, with peptide 38b and DNP-KLH Serum is collected on weeks 0, 5, 7, 9, 10, 11, 13, 16, and 20. Splenocytes are prepared from pairs of mice from each group on weeks 10 and 11.

IgG response to the peptide antigens and to DNP is monitored by conventional ELISA assays, using an anti-mouse IgG horseradish peroxidase conjugate, and microtiter plates whose wells are coated with unconjugated peptide 37 (mouse IgE-CH3 domain antigen peptide, SEQ ID NO:8) for peptide ELISA, and plates coated with DNP-BSA conjugate for DNP ELISA. Cross-reactivity of anti-37b antibodies with mouse IgE are monitored by a conventional IgG ELISA on plates coated with mouse monoclonal IgE SPE 7 (Sigma). IgG response to peptide immunogens is compared to mouse IgE crossreactivity among the groups throughout the 20 week course, to determine 1) primary and secondary responses, 2) the presence of undesirable immunosuppression of IgG responsiveness, and, 3) the occurrence of a desirable reduction in anti-IgE reactivity during weeks 10–20 as evidence of reversibility and safety of the antibody response to the peptide composition of the invention.

On weeks 7, 9, 10, 11, 13, and 16, IgE response is monitored by whole IgE ELISA and by DNP-specific ELISA. On weeks 10 and 11 splenocyte B cells that secrete IgE with specificity for DNP are enumerated by DNP-specific ELISPOT assay. Also, because serum IgE levels may not be completely predictive of anaphylaxis, i.e., IgE determinations may miss significant effects on in vivo sensitivity, sensitization of the mice is measured by Passive Percutaneous Anaphylaxis assay of mouse serum in rats (heterologous PCA). Heterologous PCA is preferred to autologous PCA assay in mice because rat skin mast cells are selectively cross-sensitized by mouse IgE as opposed to mouse IgG. Therefore, the heterologous mouse/rat PCA reaction is IgE-specific and is not confounded by IgG-mediated anaphylaxis which may occur in autologous mouse PCA assay (Maekawa and Ovary, *J Innunol Methods*, 1984; 71:229–239).

ELISA, ELISPOT, and PCA results are compared between groups for immunosuppression of IgE responsiveness and for isotypic specificity of the immunosuppression. Experimental methods are described below.

Whole IgE ELISA

For an ELISA to measure total mouse IgE in serum, microtiter plates are coated with monoclonal rat anti-mouse IgE, R35–72 (Pharmingen), at 1 μg/ml. The plates are coated, washed and blocked as described. Serially diluted mouse sera are added to the plates and incubated. Captured IgE is detected by reaction with biotinylated monoclonal rat anti-mouse IgE, R35–118 (Pharmingen), followed by sequential additions of streptavidin-horseradish peroxidase (Pierce) and OPD. $A_{492}$ values are determined.

DNP-specific IgE ELISA

For an ELISA to determine DNP hapten-specific mouse IgE in serum from mice that have been sensitized with DNP-KLH, microtiter wells are coated with DNP-BSA conjugate (Molecular Probes, Inc.) at 5 μg/ml. Captured IgE with specificity for DNP hapten is detected as described above.

DNP-specific ELISPOT

For an ELISPOT assay to determine B cells that secrete DNP hapten-specific mouse IgE, DNP-BSA conjugate at 5 μg/ml is used to coat the wells of sterile microtiter plates whose wells are lined with 0.45 μm nitrocellulose filters, for example a MULTISCREEN HA Plate (Millipore Inc., cat. no. MAHAS4510). Serially diluted splenocytes, prepared from sensitized and control mice, are added to the wells and incubated overnight at 37° C. under 5% $CO_2$. The cells are washed from the plates and IgE-secreting cells with specificity for DNP hapten are counted as localized spots on the filters following staining by alkaline phosphatase conjugated-rat monoclonal antibody R35–118 with 5-bromo-4-chloro-3-indoyl phosphate (Sigma) as colored substrate.

Heterologous PCA

Serial dilutions of sera from immunized/sensitized and control mice are injected intradermally into the shaved backs of adult male Sprague-Dawley rats. Anesthetized animals receive 10–12 injections of diluted serum into each of three parallel rows on the dorsal skin (50 μl/site). Each pattern of injections is replicated in duplicate animals. After a 24 hour latent period, for effective sensitization of skin mast cells, rats are challenged by intravenous injection of 1 mg of DNP-BSA in 1% Evans blue dye in PBS. In 30 minutes to 1 hour, rats are asphyxiated and skinned so that blueing reactions can be observed on the inside of the dorsal skin. A PCA titer is determined from the highest serum dilution which results in a readily definable spot.

EXAMPLE 6

Immunization of Mice and Inhibition of Passive Cutaneous Anaphylaxis

To study the effect of immunization by an immunogenic peptide of the invention on an IgE-mediated inflammatory reaction, an antibody response was elicited to the mouse IgE-CH3 target antigenic site, SEQ ID NO:8, by immunizing mice with a peptide of the invention. The resulting mouse antiserum was then used to suppress the passive cutaneous anaphylaxis (PCA) triggered by the crosslinking of mouse IgE bound to rat mast cells.

Materials and Methods

Balb/c mice were immunized with a peptide composition of the invention, SEQ ID NO:25, as described in Example 5, except that the subcutaneous injections were given on weeks 0, 3, and 6 only and the mice were not sensitized. On week 8, mouse sera were collected and evaluated for crossreactivity to IgE by mouse IgE ELISA. The mouse IgE ELISA was as described for the human IgE ELISA in Example 1 except that microtiter wells were coated with 1 μg/ml of mouse anti-DNP IgE monoclonal antibody SPE7 (Sigma Chemical Co., St. Louis Mo.), and horseradish peroxidase (HRP)-labeled goat anti-mouse IgG (Kirkegaard and Perry Laboratories, Gaithersburg Md.) was used for detection of captured mouse IgG. Thirteen out of 20 immunized mice had crossreactive antibodies for mouse IgE. Sera was pooled from seven mice showing ELISA titers against mouse IgE of $>\log_{10}$ 2.3 for use as the site-specific anti-IgE.

Another group of 10 balb/c mice was used to produce murine IgE. This group was sensitized by a single intraperitoneal administration of ovalbumin (Oa) on 0.4% Alum, 1.0 μg/0.2 ml. IgE content of the mouse sera was measured at day 20 by the whole IgE ELISA described in Example 5, except that captured IgE was detected by HRP-labeled sheep anti-mouse IgE supplied by The Binding Site Inc. (San Diego, Calif.). Out of the 10 mice, 7 had appreciable IgE responses of titer $>\log_{10}$ 1.6. These sera were pooled for use as the anti-Oa IgE working stock.

The IgE serum pool was serially diluted 1:62, 1:124 and 1:248 into PBS and then further diluted with an equal volume of the site-specific anti-IgE serum. Thus, final dilutions for mouse IgE were 1:124, 1:248, and 1:496 while mouse anti-IgE was diluted 1:2. Control dilutions of IgE were prepared having only PBS as diluent.

The IgE dilutions, with and without anti-IgE serum, were incubated for 1 hour at 37° and 50 μl of each was taken for evaluation by heterologous PCA reaction.

Results

The 50 μl samples of diluted mouse IgE were injected intradermally into the shaved back-of rats in a pattern that was a set of two rows of four injections. The rows were a row of three controls of IgE diluted 1:124, 1:248, and 1:496 in PBS only; in parallel with a row of the serially diluted IgE incubated with the site-specific anti-IgE. The fourth injection of each row was PBS only, as a control for the tissue trauma. The pattern was duplicated on two rats.

After 24 hours, PCA reactions were induced by intravenous injection of 1 mg of DNP-Oa conjugate in 1% Evans blue dye. One hour later, the rats were euthanized and skinned. The DNP-Oa allergen had crosslinked receptor-bound mouse anti-Oa IgE on the rat mast cells. The crosslinking triggered degranulation, increased permeability of the Evans blue dye, and the appearance of blue zones on the underside of the rat skins proportional to the extent of degranulation. However, wherever free IgE had been depleted by the site-specific murine anti-IgE, less was available to sensitize the rat mast cells and PCA reactions were suppressed. PCA reactions were evaluated by measuring the diameters of the blue zones on the undersides of the rat skins in two directions at right angles and taking the average. Results are shown in Table 7 for the duplicate inhibition of PCA determinations on two rats.

The rats differed by their inherent sensitivities to the mouse IgE so that control and anti-IgE inhibited PCA reactions should be compared only on the same rat. Mouse IgE-mediated PCA reactions were inhibited in both rats by the murine antiserum with specificity for the target antigenic site on mouse IgE. Thus, the antibody response that results from immunization by a peptide composition specific for the target antigenic site of a non-human IgE resulted in suppression of the inflammatory response mediated by the selfsame non-human IgE.

TABLE 1

Sequence

```
                224         230                    240                  250   253b        260
Human ε         V C S R D F T P P T V K I L Q S S - C D G G G H F - P P T I Q L L C L V S G Y T P G T Z N Z
(Seq ID No: 1)
Dog ε           A C A L N F I P P T V K L F H S S - C N - P V G D T H T T I Q L L C L I S G Y V P G D M E V
(Seq ID No: 2)
Rat ε           A R P V N I T K P T V D L L H S S - C D - P N A F - H S T I Q L Y C F V Y G H I Q N D V S I
(Seq ID No: 3)
Mouse ε         V R P V T H S L S P P W S Y S I H R C D - P N A F - H S T I Q L Y C F I Y G H I L N D V S V
(Seq ID No: 4)

270                 280                    290                   300                   310
Human ε         T W L E D G Q - V M D V D L S T A - S T T Q E G E L A S T Q S E L T L S Q K H W L S D R T Y
(Seq ID No: 1)
Dog ε           I W L V D G Q K A T N I F P Y T A P G T K - E G N V T S T H S E L N I T Q G E W V S Q K T Y
(Seq ID No: 2)
Rat ε           H W L M D D R K I Y D T H A Q N V - L I K E E G K L A S T Y S R L N I T Q Q Q W M S E S T F
(Seq ID No: 3)
Mouse ε         S W L M D D R E I T D T L A Q T V - L I K E E G K L A S T C S K L N I T E Q Q W M S E S T F
(Seq ID No: 4)

320                  330                   340                  350
Human ε         T C Q V - T Y Q G H T F E D S T K K C A D S N P R G V S A Y L S R P S P F D L F I R K S P T
(Seq ID No: 1)
Dog ε           T C Q G F T F K D E A R K - - - - - C S E S D P R G V T S Y L S P P S P L D L Y V H K A P K
(Seq ID No: 2)
Rat ε           T C K V - T S Q G E N Y W A H T R R C S D D E P R G V I T Y L I P P S P L D L Y E N G T P K
(Seq ID No: 3)
Mouse ε         T C R V - T S Q G C D Y L A H T R R C P D H E P R G A I T Y L I P P S P L D L Y Q N G A P K
(Seq ID No: 4)

360               370                  380                 390
Human ε         I T C L V V D L A P S K G T V N L T W S R A S G K P - V N H S T R K E E K Q R - N G T L T
(Seq ID No: 1)
Dog ε           I T C L V V D L A T M E G M - N L T W Y R E S K E P - V N P G P L N K - K D H F N G T I T
(Seq ID No: 2)
Rat ε           L T C L V L D L E S E E - N I T V T W V R E R K K S I G S A S Q R S T - K H H - N A T T S
(Seq ID No: 3)
Mouse ε         L T C L V V D L E S E - K N V N V T W N Q E - K K T S V S A S Q W Y T - K H H N N A T T S
(Seq ID No: 4)
```

TABLE 1-continued

```
                400            410            420            430            440
Human ε     V T S T L P V G T R D W I E G E T Y Q C R V T H P H L P R A L M R S T T K T - S G P R A A P
(Seq ID No: 1)
Dog ε       V T S T L P V N T N D W I E G E T Y Y C R V T H P H L P K D I V R S I A K A - P G K R A P P
(Seq ID No: 2)
Rat ε       I T S I L P V D A K D W I E G E G Y Q C R V D H P H F P K P I V R S I T K A - L G L R S A P
(Seq ID No: 3)
Mouse ε     I T S I L P V V A K D W I E G Y G Y Q C I V D R P D F P K P I V R S I T K T Q P G Q R S A P
(Seq ID No: 4)

450            460            470            480
Human ε     E V Y A F A T P E W P G S R D K - R - T L A C L I Q N F M P E D I S V Q W L H N E V Q L P D
(Seq ID No: 1)
Dog ε       D V Y L F L P P E - E E Q G T K D R V T L T C L I Q N F F P A D I S V Q W L R N D S P I Q T
(Seq ID No: 2)
Rat ε       E V Y V F L P P E - E E K N K - R - T L T C L I Q N F F P E D I S V Q W L Q D S K L I P K
(Seq ID No: 3)
Mouse ε     E V Y V F P P P E - E E S E D K - R - T L T C L I Q N F F P E D I S V Q W L G D K L I S N
(Seq ID No: 4)

490            500            510            520
Human ε     A R H S T T Q - P R K T K G S - - G F F V F S R L E V T R A E W - Q E K D E F I C R A V H E
(Seq ID No: 1)
Dog ε       D Q Y - T T T G P H K V S G S R P A F F I F S R L E V S R V D W E Q - K N K F T C Q V V H E
(Seq ID No: 2)
Rat ε       S Q H S T T T - P L K T N G S N Q R F F I F S R L E V T K A L W T Q T K Q - F T C R V I H E
(Seq ID No: 3)
Mouse ε     S Q H S T T T - P L K S N G - N Q G F F I F S R L E V A K T L W T Q R K Q - F T C Q V I H E
(Seq ID No: 4)

530            540
Human ε     A A S P S Q T V Q R A V S V N P G K
(Seq ID No: 1)
Dog ε       A L S G S R
(Seq ID No: 2)
Rat ε       A L R E P R
(Seq ID No: 3)
Mouse ε     A L Q K P R
(Seq ID No: 4)
```

TABLE 2

Screening of IgE CH2/3 Peptides for Selection of Candidate IgE Antigens

| | Entry No.; Description† | IgE Derived Target Antigenic Site Amino Acid Sequence | | Immunostimulatory sequence attached to Target Antigenic Site | Cross-reactivity with human IgE $Log_{10}$ ELISA Titer vs HuIgE |
|---|---|---|---|---|---|
| 1 | CH2/3 (328–376) ($C_{350} \rightarrow S$) | CADSNPRGVSAYLSRPSPFDLFIRKSPTITSLVVDLAPSKGTVN LTWSR (SEQ ID NO:28) | a | KLH | 3.66 |
| 2 | CH2/3 (317–376) ($C_{350} \rightarrow S$) | QGHTFEDSTKKCADSNPRGVSAYLSRPSPFDLFIRKSPTITSLVV DLAPSKGTVNLTWSR (SEQ ID NO:29) | a b | KLH 1,4,9 Palindromic Th lib-GG | 5.08 3.77 |

TABLE 2-continued

Screening of IgE CH2/3 Peptides for Selection of Candidate IgE Antigens

| IgE Derived Target Antigenic Site | | | Immunostimulatory sequence attached | | Cross-reactivity with human IgE $Log_{10}$ ELISA |
|---|---|---|---|---|---|
| Entry No.; | Description† | Amino Acid Sequence | to Target Antigenic Site | | Titer vs HuIgE |
| 3 | CH2/3 (313–376) ($C_{350}\rightarrow$S) | QVTYQGHTFEDSTKKCADSNPRGVSAYLSRPSPFDLFIRKSPTITSLVVDLAPSKGTVNLTWSR (SEQ ID NO:30) | a | KLH | 3.12 |
| 4 | CH2/3 (301–376) ($C_{350}\rightarrow$S) | QKHWLSDRTYTSQVTYQGHTFEDSTKKCADSNPRGVSAYLSRPSPFDLFIRKSPTITSLVVDLAPSKGTVNLTWSR (SEQ ID NO:31) | a | KLH | 4.04 |
| 5 | CH2/3 (328–362) ($C_{350}\rightarrow$S) | CADSNPRGVSAYLSRPSPFDLFIRKSPTITSLVVD (SEQ ID NO:32) | a | KLH | 4.40 |
| 6 | CH2/3 (317–362) ($C_{350}\rightarrow$S) | QGHTFEDSTKKCADSNPRGVSAYLSRPSPFDLFIRKSPTITSLVVD(SEQ ID NO:33) | a | KLH | 4.30 |
| 7 | CH2/3 (313–362) ($C_{350}\rightarrow$S) | QVTYQGHTFEDSTKKCADSNPRGVSAYLSRPSPFDLFIRKSPTITSLVVD (SEQ ID NO:34) | a | KLH | 3.92 |
| 8 | CH2/3 (301–362) ($C_{350}\rightarrow$S) | QKHWLSDRTYTSQVTYQGHTFEDSTKKCADSNPRGVSAYLSRPSPFDLFIRKSPTITSLVVD (SEQ ID NO:35) | a | KLH | 3.37 |
| 9 | CH2/3 (328–356) | CADSNPRGVSAYLSRPSPFDLFIRKSPTI (SEQ ID NO:36) | a | KLH | 3.49 |
| 10 | CH2/3 (317–356) | QGHTFEDSTKKCADSNPRGVSAYLSRPSPFDLFIRKSPTI (SEQ ID NO:37) | a | KLH | 4.71 |
| | | | b | HBs$_{19-32}$Th-GG | 3.76 |
| | | | c | Inv-GG-HBs$_{19-32}$ Th-GG | 2.94 |
| 11 | CH2/3 (313–356) | QVTYQGHTFEDSTKKCADSNPRGVSAYLSRPSPFDLFIRKSPTI (SEQ ID NO:38) | a | KLH | 4.31 |
| 12 | CH2/3 (301–356) ($C_{312}\rightarrow$S) | QKHWLSDRTYTSQVTYQGHTFEDSTKKCADSNPRGVSAYLSRPSPFDLFIRKSPTI (SEQ ID NO:39) | a | KLH | 2.79 |
| 13 | CH2/3 (301–376) | QKHWLSDRTYTCQVTYQGHTFEDSTKKCADSNPRGVSAYLSRPSPFDLFIRKSPTITCLVVDLAPSKGTVNLTWSR (SEQ ID NO:40) | a | KLH | 3.77 |
| 14 | (C)CH3 (391–398) (C)* | (C)KQRNGTLT(C) (SEQ ID NO:41) | b | HBS$_{19-32}$Th-GG | 1.47 |
| | | | c | Inv-GG-HBs$_{19-32}$Th-GG | 0.77 |
| | | | c | Inv-GG-HBs$_{19-32}$Th-GG | 0.77 |
| 15 | (C)CH3 (413–435) (C)* ($C_{418}\rightarrow$S) | (C)GETYQSRVTHPHLPRALMRSTTK(C) (SEQ ID NO:5) | b | Syn Th (1,2,4) GG | 4.24 |
| | | | c | Inv-GG-Syn Th (1,2,4)-GG | 4.17 |
| 16 | CH2/3 (301–345) | QKHWLSDRTYTCQVTYQGHTFEDSTKKCADSNPRGVSAYLSRPSP (SEQ ID NO:42) | b | HBs$_{19-32}$Th-GG | 2.31 |
| 17 | (C)CH3 (365–396) (C)* | (C)PSKGTVNLTWSRASGKPVNHSTRKEEKQRNGT(C) (SEQ ID NO:43) | b | HBs$_{19-32}$Th-GG | <1.0 |
| 18 | (C)CH3 (404–434) (C)* | (C)PVGTRDWIEGETYQCRVTHPHLPRALMRSTT(C) (SEQ ID NO:44) | b | HBs$_{19-32}$Th-GG | <1 |
| 19 | CH3 (432–445) | STTKTSGPRAAPEV (SEQ ID NO:45) | b | HBs$_{19-32}$Th-GG | 2.725 |
| 20 | (C)CH3(374–382-(C)-383–385)* | (C)WSRASGKPV(C)NHS (SEQ ID NO:46) | b | HBs$_{19-32}$Th-GG | 3.976 |
| 21 | CH3 (345–357)* | (C)PSPFDLFIRKSPT(C) (SEQ ID NO:83) | b | HBs$_{19-32}$Th-GG | $<1^{\Delta}$ |
| | | | c | Inv-GG-HBs$_{19-32}$ Th-GG | |
| 22 | (C)CH3 (343–360)* | (C)SRPSPFDLFIRKSPTITC (SEQ ID NO:47) | b | HBs$_{19-32}$Th-GG | $<1^{\Delta}$ |
| | | | c | Inv-GG-HBs$_{19-32}$ Th-GG | |
| 23 | (C)CH3 (404–413) (P) (C)* | (C)VGTRDWIEGE(P)(C) (SEQ ID NO:48) | b | HBs$_{19-32}$Th-GG | $<1^{\Delta}$ |
| | | | c | Inv-GG-HBs$_{19-32}$ Th-GG | |
| 24 | (C)(P)CH3 (403–413) (P)(C)* | (C)(P)PVGTRDWIEGE(P)(C) (SEQ ID NO:49) | b | HBs$_{19-32}$Th-GG | $<1^{\Delta}$ |
| | | | c | Inv-GG-HBs$_{19-32}$ Th-GG | |
| 25 | (C)CH3 (387–400) (C)* | (C)KEEKQRNGTLTVTS(C) (SEQ ID NO:50) | b | HBs$_{19-32}$Th-GG | $<1^{\Delta}$ |
| | | | c | Inv-GG-HBs$_{19-32}$ Th-GG | |
| 26 | CH3 (387–394) | KEEKQRNG (SEQ ID NO:52) | b | HBs$_{19-32}$Th-GG | <1 |
| | | | c | Inv-GG-HBs$_{19-32}$ Th-GG | |
| 27 | (C)CH3 (373–381) (C)* | (C)WSRASGKPV(C) (SEQ ID NO:52) | b | HBs$_{19-32}$Th-GG | $2.40^{\Delta}$ |
| | | | c | Inv-GG-HBs$_{19-32}$ Th-GG | |

TABLE 2-continued

Screening of IgE CH2/3 Peptides for Selection of Candidate IgE Antigens

| Entry No.; Description† | IgE Derived Target Antigenic Site | | Immunostimulatory sequence attached to Target Antigenic Site | | Cross-reactivity with human IgE $Log_{10}$ ELISA Titer vs HuIgE |
|---|---|---|---|---|---|
| | | Amino Acid Sequence | | | |
| 28 | CH3 (354–373) (C)* | PTITCLVLDLAPSKGTVNLT(C) (SEQ ID NO:53) | b | $HBs_{19-32}$Th-GG | 2.59 |
| 29 | CH3 (354–369) | PTITCLVLDLAPSKGT (SEQ ID NO:54) | b | $HBs_{19-32}$Th-GG | 2.39 |
| 30 | CH3 (399–424) | TSTLPVGTRDWIEGETYQCRVTHPH (SEQ ID NO:55) | b | $HBs_{19-32}$Th-GG | 4.01 |
| 31 | CH3 (354–368)(C)* ($C_{350}$→S) ($D_{352}$→C) | PTITSLVLCLAPSKG(C) (SEQ ID NO:56) | b | $HBs_{19-32}$Th-GG | <1 |
| 32 | (C)CH3 (370–390) (C)* | (C)VNLTWSRASGKPVNHSTRKEE(C) (SEQ ID NO:57) | b | $HBs_{19-32}$Th-GG | 3.45 |
| 33 | (C)CH3 (373–424)* | (C)TWSRASGKPVNHSTRKEEKQRNGTLTVTSTLPVGTRDW IEGETYQCRVTHPH (SEQ ID NO:58) | b | $HBs_{19-32}$Th-GG | 2.33 |
| 34 | CH4 (497–506) | KTKGSGFFVF (SEQ ID NO:59) | b | $HBs_{19-32}$Th-GG + $MVF_{288-302}$Th-GG + $PT_{149-176}$Th-GG | <1 |

*= cyclized peptide
†= amino acid residue numbers form Table 1, SEQ ID No. 1
Δ= crossreactivity results are for a mixture of "b" and "c" peptides
c→ cysteine introduced into native sequence for cyclization
CΔS= Serine substituted for cysteine residue,
D→C= cysteine substituted for aspartic acid residue.

TABLE 3

Evaluation of Anti-IgE Antibodies for Inhibition of Histamine Release

| IgE Antigen Entry No. | IgE Antigen Description (SEQ ID NO) | | Immunogenic Elements Attached to IgE Antigen | % Inhibition of Histamine Release† |
|---|---|---|---|---|
| 1 | CH2/3 (328–376) ($C_{358}$–S) (SEQ ID NO:28) | a | KLH | 0 |
| 2 | CH2/3 (317–376) ($C_{358}$–S) (SEQ ID NO:29) | a b | KLH 1,4,9 PALINDROMIC Th-GG- | 14% 17% and 0 |
| 5 | CH2/3 (328–362) ($C_{358}$–S) (SEQ ID NO:32) | a | KLH | 0 |
| 6 | CH2/3 (317–362) ($C_{358}$–S) (SEQ ID NO:33) | a | KLH | 0 |
| 7 | CH2/3 (313–362) ($C_{358}$–S) (SEQ ID NO:34) | a | KLH | 6% |
| 8 | CH2/3 (301–362) ($C_{358}$–S) (SEQ ID NO:35) | a | KLH | 6% |
| 11 | CH2/3 (313–356) (SEQ ID NO:38) | a | KLH | 6% |
| 15 | (C)CH3 (413–435)(C)* ($C_{418}$→S) (SEQ ID NO:5) | b c | Syn Th(1,2,4)-GG Inv-GG-Syn Th(1,2,4)-GG- | 58%' and 71%-⊕ |
| 20 | (C)CH3 (374–382-(C)-383–385)* (SEQ ID NO:46) | b | $HBs_{19-32}$Th-GG | 0 |
| 30 | CH3 (399–424) (SEQ ID NO:55) | b | $HBs_{19-32}$Th-GG- | 9% and 0 |
| 32 | (C)CH3 (370–390)(C)* (SEQ ID NO:57) | b | $HBs_{19-32}$Th-GG- | 0 |

*Cyclized peptide
(C) Cysteine introduced into native sequence for cyclization
(C–S) Serine substituted for cysteine residue
‡Results are shown for pooled anti-15b and anti-15c IgG's.
†Histamine release inhibition by antibodies to peptides, purified from serum collected at week 8, except as otherwise noted ⊕
⊕Histamine release inhibition by antibodies to peptides, collected at week 12.

TABLE 4A

| IgE-CH3 antigen SEQ ID NO | Description, SEQ ID NO(S) of immunostimulatory sequence | Amino acid sequence and SEQ ID NO of peptide |
|---|---|---|
| SEQ ID NO:5 | Syn Th(1,2,4)-GG-<br>SEQ ID NO:9 | KKKIITITRIITIITTIDGGCGETYQSRVTHPHLPRALMRSTTKC<br>(SEQ ID NO:14) |
| SEQ ID NO:5 | Inv-GG-Syn Th(1,2,4)-GG-<br>SEQ ID NOS:13, 9 | TAKSKKFPSYTATYQFGGKKKIITITRIITIITTIDGGCGETYQSRVTHPHLPRALMRSTTKC<br>(SEQ ID NO:15) |
| SEQ ID NO:5 | CT P11 Th-GG-Syn Th(1,2,4)1-GG-<br>SEQ ID NOS:12, 9 | TINKPKGYVGKEGGKKKIITITRIITIITTIDGGCGETYQSRVTHPHLPRALMRSTTKC<br>(SEQ ID NO:17) |
| SEQ ID NO:5 | IS(1,4,9 PAL†)LF simplified Th-GG-<br>SEQ ID NO:60 | ISISEIKGVIVHKIEGILFGGCGETYQSRVTHPHLPRALMRSTTKC<br>   T  RT   TR  T<br>(SEQ ID NO:18) |
| SEQ ID NO:5 | Inv-IS(1,4,9 PAL†)LF simplified Th-GG-<br>SEQ ID NOS:13, 60 | TAKSKKFPSYTATQFGGISISEIKGVIVHKIEGILFGGCGETYQSRVTHPHLPRALMRSTTKC<br>                         T  RT   TR  T<br>(SEQ ID NO:19) |
| SEQ ID NO:5 | (CT P11 Th)-GG-IS(1,4,9 PAL†)LF simplified Th-GG-<br>SEQ ID NOS:12, 60 | TINKPKGYVGKEGGISISEIKGVIVHKIEGILFGGCGETYQSRVTHPHLPRALMRSTTKC<br>TINKPKGYVGKEGGISISEIKGVIVHKIEGILFGGCGETYQSRVTHPHLPRALMRSTTKC<br>(SEQ ID NO:20) |
| SEQ ID NO:5 | (1,4,9 PAL†) Th-GG-<br>SEQ ID NO:10 | ISEIKGVIVHKIEGIGGCGETYQSRVTHPHLPRALMRSTTKC<br>MT  RT    TRM TM<br>L  L   V<br>(SEQ ID NO:21) |
| SEQ ID NO:5 | Inv-(1,4,9 PAL†) Th-GG-SEQ ID NOS:13, 10 | TAKSKKFPSYTATYQFGGISEIKGVIVHKIEGIGGCGETYQSRVTHPHLPRALMRSTTKC<br>                    MT  RT    TRM TM<br>                    L  L   V<br>(SEQ ID NO:22) |
| SEQ ID NO:5 | (CT P11 Th)-(1,4,9 PAL †)Th-GG-SEQ ID NOS: 12, 10 | TINKPKGYVGKEGGISEIKGVIVHKIEGIGGCGETYQSRVTHPHLPRALMRSTTKC<br>              MT  RT    TRM TM<br>              L  L   V<br>(SEQ ID NO:23) |
| SEQ ID NO:5 | CTR11Th-GG-IS(1,4,9, PAL†)LF simplified Th-GG-<br>SEQ ID NOS: 12, 60 | TINKPKGYVGKEGGISISEIKGVIVHKIEGILFGGCGETTYQSRVTHPHLPRALMRSTTKC<br>              T  RT   TR  T<br>(SEQ ID NO:85) |
| SEQ ID NO:5 | klh*-KKK- | [klh*]-KKKCGETYQSRVTHPHLPRALMRSTTKC |
| SEQ ID NO:8 | klh*-KKK- | [klh*]-KKKCGYGYQSIVDRPDFPKPIVRSITKC |
| SEQ ID NO:8 | IS(1,4,9 PAL†)LF simplified Th-GG-<br>SEQ ID NO:60 | ISISEIKGVIVHKIEGILFGGCGYGYQSIVDRPDFPIVRSITKC<br>   T  RT   TR  T<br>(SEQ ID NO:24) |
| SEQ ID NO:8 | Syn Th(1,2,4)-GG-<br>SEQ ID NO:9 | KKKIITITRIITIITTIDGGCGYGYQSIVDHPDFPKPIVRSITKC<br>(SEQ ID NO:25) |
| SEQ ID NO:6 | klh*-KKK- | [klh*]-KKKCGETYYSRVTHPHLPKDIVRSIAKC |
| SEQ ID NO:6 | Syn Th(1,2,4)-GG-<br>SEQ ID NO:9 | KKKIITIRIITIITTIDGGCGETYYSRVTHPHLPKDIVRSIAKC<br>(SEQ ID NO:26) |
| SEQ ID NO:6 | IS(1,4,9 PAL †)LF Th-GG-SEQ ID NO:11 | ISISEIKGVIVHKIEGILFGGCGETYYSRVTHPHLPKDIVRSIAKC<br>MT     RT    TRM TM<br>L    L  V<br>(SEQ ID NO:27) |
| SEQ ID NO:6 | SMTPITh- K-Syn Th (1,2,3)- K-SEQ ID NOS:86,60 | KWFKTNAPNGVDEKIRIεKKKKIITITRIITIITTIDεKCGETYYSRVTHPHLPKDIVRSIAKC<br>(SEQ ID NO:87) |
| SEQ ID NO:6 | CTP11Ph-εK-Syn Th(1,2,4)-εK-SEQ ID NOS:12, 9 | TINKPKGYVGKEεKKKKIITITRIITIITTIDεKCGETYYSRVTHPHLPKDIVRSIAKC<br>(SEQ ID NO:88) |

TABLE 4A-continued

| IgE-CH3 antigen SEQ ID NO | Description, SEQ ID NO(S) of immunostimulatory sequence | Amino acid sequence and SEQ ID NO of peptide |
|---|---|---|
| SEQ ID NO:6 | ArtMVFTh-εK-SEQ ID NO:89 | ISLTEIRTVIVTRLETVLFεKCGETYYSRVTHPHLPKDIVRSIAKC (SEQ ID NO:90) |
| SEQ ID NO:6 | SMTPITh-εK-ArtMVFTh-εK-SEQ ID NOS:86, 89 | KWFKTNAPNGVDEKIRIεKISLTEIRTVIVTRLETVLFεKCGETYYSRVTHPHLPKDIVRSIAKC (SEQ ID NO:91) |

*klh = keyhole limpet hemocyanin, chemically linked (see Example 1)
†PAL = Palindromic

TABLE 4B

Immunogenicity of Representative Peptide Constructs of the Invention

| | SEQ ID NO of peptide contructs | Species immunized | Site-directed crossreactivity to IgE ($Log_{10}$ titer) | % $HR^c$ | % $HR^d$ inhibition |
|---|---|---|---|---|---|
| Human IgE Target | SEQ ID NO:18 | $GP^a$ | $4.4^e$ | 1 | 96 |
| | SEQ ID NO:85 | $GP^a$ | $4.2^e$ | 3 | 87 |
| | SEQ ID NO:18 | $Pig^a$ | $4.1^e$ | 3 | 84 |
| | SEQ ID NO:18 | $Baboon^a$ | $4.8^e$ | 8 | 53 |
| Dog IgE Target | SEQ ID NO:87 | $GP^b$ | $3.4^f$ | NT | NT |
| | SEQ ID NO:88 | $GP^c$ | $3.2^f$ | NT | NT |
| | SEQ ID NO:90 | $GP^b$ | $3.2^f$ | NT | NT |
| | SEQ ID NO:91 | $GP^b$ | $3.2^f$ | NT | NT |

$^a$Guinea pigs, pigs and baboon were immunized with human IgE peptide constructs at 0, 3 and 6 weeks, with sera collected at 8 wpi for testing by human IgE ELISA and inhibition of HR.
$^b$Guinea pigs were immunized with dog IgE peptide constructs at 0, 2 and 4 weeks with sera collected at 6 wpi for dog IgE ELISA.
$^c$Average % HR.
$^d$% HR inhibition = control - % HR/control x 100
GP Guinea pig
NT Not tested

TABLE 5

Amino Acid Sequences of Foreign Pathogen-Derived Th Epitopes

| Description of Th | SEQ ID NO | Amino Acid Sequences |
|---|---|---|
| $MVF_{288-302}$ Th | 61 | LSEIKGVIVKRLEGV |
| $MVF_{258-277}$ Th | 62 | GILESRGIKARITHVDTESY |
| $TT_{830-844}$ Th | 63 | KKQYIKANSKFIGITEL |
| $TT_{947-966}$ Th | 64 | KKFNNFTVSFWLRVPKVSASHL |
| $PT_{149-176}$ Th | 65 | KKLRRLLYMIYMSGLAVRVHVSKEEQYYDY |
| $TT_{73-99}$ Th | 66 | YDPNYLRTDSDKDRFLQTMVKLFNRIK |
| $PT_{18-41}$ Th | 67 | GAYARCPNGTRALTVAELRGNAEL |
| $HBs_{15-32}$ Th | 68 | FFLLTRILTIPQSLD |
| $HBc_{120-140}$ Th | 69 | VSFGVWIRTPPAYRPPNAPIL |
| $HBc_{23-40}$ Th | 70 | SDFFPSVRDLLDTASALYRE |
| $HBc_{50-69}$ Th | 71 | PHHTALRQAILCWGELMTLA |
| $TT_{615-631}$ Th | 72 | WVRDIIDDFTNESSQKT |
| HIV gp41 $Th_6$ (N—) | 73 | RAGRAILHIPTRIRQGLER |
| HIV gp41 $Th_6$ (C—) | 74 | AVAEGTDRVIEVLQRAGRAIL |
| CT $A8_{106-130}$ Th | 75 | ALNIWDRFDVFTLGATSGYLKGNS |
| CT P11 Th | 12 | TINKPKGYVGKE |
| DT1 Th | 76 | DSETADNLEKTVAALSILPGHG |
| DT4 Th | 77 | EEIVAQSIALSSLMVAQAIPLVGELVDIGFAATNFVESC |
| PF Th | 78 | DIEKKTIAKMEKASSVFNVVNS |
| SM Th | 79 | KWFKTNAPNGVDEKIRI |
| TraT1 Th | 80 | GLQGKIADAVKAKG |
| TraT4 Th | 81 | GLAAGLVGMAADAMVEDVN |
| TraT6 Th | 82 | STETGNQHHYQTRVVSNANK |
| SMTPITh | 86 | KWFKTNAPNGVDEKIRI |

TABLE 6

Amino Acid Sequences of Representative Artificial Th Epitopes and SSAL

| Description of Th | SEQ ID NO: | Amino Acid Sequence |
|---|---|---|
| (1,4,9 PALINDROMIC) Th | 10 | ISEIKGVIVHKIEGI<br>MT  RT   TRM TM<br>L   L    V |
| Syn Th(1,2,4) | 9 | KKKIITITRIITIIITTID |
| IS(1,4,9 PALINDROMIC)LF simplified Th | 60 | ISISEIKGVIVHKIEGILF<br>T  RT   TR  T |
| IS(1,4,9 PALINDROMIC)LF Th | 11 | ISISEIKGVIVHKIEGILF<br>MT  RT   TRM TM<br>L   L    V |
| ArtMVF Th | 89 | ISLTEIRTVIVTRLETVLF |

TABLE 7

Inhibition of PCA Reaction

| IgE Dilution | Rat #5 | | Rat #6 | |
|---|---|---|---|---|
| | No Anti-IgE (mm) | Anti-IgE 1:2 (mm) | No Anti-IgE (mm) | Anti-IgE 1:2 (mm) |
| 0 | 0 | 0 | 0 | 0 |
| 1:496 | 0 | 0 | 4.3 | 0 |
| 1:248 | 0 | 0 | 7.0 | 6.0 |
| 1:124 | 11 | 4* | 13.0 | 12.7 |

*very pale blue

What is claimed is:

1. An IgE-CH3 domain antigen peptide of between about 25 and about 29 amino acids in length containing two cysteine residues separated by about 23 amino acid residues, selected from the group consisting of SEQ ID NO:5, SEQ ID NO:6, SEQ ID NO:7, SEQ ID NO:8, and SEQ ID NO:84, or an immunologically functional analog thereof, wherein from one to four of the residues in SEQ ID NO:5 is conservatively substituted or deleted.

2. The IgE-CH3 domain antigen peptide of claim 1 selected from the group consisting of SEQ ID NO:5, SEQ ID NO:6, SEQ ID NO:7, SEQ ID NO:8, and SEQ ID NO:84.

3. A peptide conjugate comprising a carrier protein covalently attached to one or more IgE-CH3 domain antigen peptides according to claim 1.

4. The peptide conjugate of claim 3 wherein the carrier protein is keyhole limpet hemocyanin.

* * * * *